United States Patent
Masychev

[19]

[11] Patent Number: 6,123,719
[45] Date of Patent: Sep. 26, 2000

[54] DIAGNOSTIC APPARATUS UTILIZING RADIATION INTERACTION WITH BIOLOGICAL TISSUE

[75] Inventor: Victor Masychev, Moscow, Russian Federation

[73] Assignee: Rosslyn Medical Limited, London, United Kingdom

[21] Appl. No.: 09/065,031
[22] PCT Filed: Oct. 24, 1996
[86] PCT No.: PCT/GB96/02604
§ 371 Date: Apr. 23, 1998
§ 102(e) Date: Apr. 23, 1998
[87] PCT Pub. No.: WO97/15226
PCT Pub. Date: May 1, 1997

[30] Foreign Application Priority Data

Oct. 24, 1995 [GB] United Kingdom .................... 9521784

[51] Int. Cl.[7] ........................................... A61B 6/00
[52] U.S. Cl. ............................................. 607/407
[58] Field of Search ................................ 600/310, 312, 600/321, 342, 407

[56] References Cited

U.S. PATENT DOCUMENTS

| 4,072,858 | 2/1978 | Stone ...................................... 250/205 |
| 4,655,225 | 4/1987 | Dahne et al. ........................... 128/633 |
| 4,768,513 | 9/1988 | Suzuki .................................... 128/634 |
| 4,991,954 | 2/1991 | Akiyama ................................ 351/221 |
| 5,227,969 | 7/1993 | Waggener et al. .................. 364/413.26 |

FOREIGN PATENT DOCUMENTS

| 003015 | 7/1979 | European Pat. Off. . |
| 441394 | 8/1991 | European Pat. Off. . |
| 650694 | 5/1995 | European Pat. Off. . |
| 2650890 | 8/1989 | France . |
| 3137326 | 3/1983 | Germany . |
| 3718202 | 11/1988 | Germany . |
| 57-37763 | 3/1982 | Japan . |
| 60-83990 | 4/1985 | Japan . |
| 9013091 | 11/1990 | WIPO . |

OTHER PUBLICATIONS

Stringer et al., "In vivo monitoring of photosensitiser fluorescence during photodynamic therapy," SPIE vol. 2371, pp. 104–108.

Yang et al., "A new method for clinical detection of cancer by rapidly analyzing the argon laser induced autofluorescence spectra," SPIE vol. 1616, 1991, pp. 82–89.

International Search Report.

*Primary Examiner*—William E. Kamm
*Attorney, Agent, or Firm*—Biebel & French

[57] ABSTRACT

A diagnostic apparatus comprises a source (1) of probing electromagnetic radiation and means (2) for transmitting the output from the probing radiation source (1) to biological tissue (3) to be examined. The apparatus also comprises means (4, 41) for detecting probing radiation reflected from the tissue (3) and stimulated radiation resulting from excitation of the tissue (3) by the probing radiation. A processing means (5–9) responsive to the reflected and stimulated radiations to produce a signal for diagnosis of the condition of the tissue and means (15, 16) for regulating the intensity of the probing radiation including a feedback circuit (16, 17, 18) for controlling the regulating means (15) and responsive to the intensity of the probing, reflected and/or stimulated radiation are also included.

44 Claims, 27 Drawing Sheets

THE CENTRE OF THE INFILTRATE

THE BORDERS OF THE INFILTRATE 2 cm FROM THE BORDER OF THE INFILTRATE

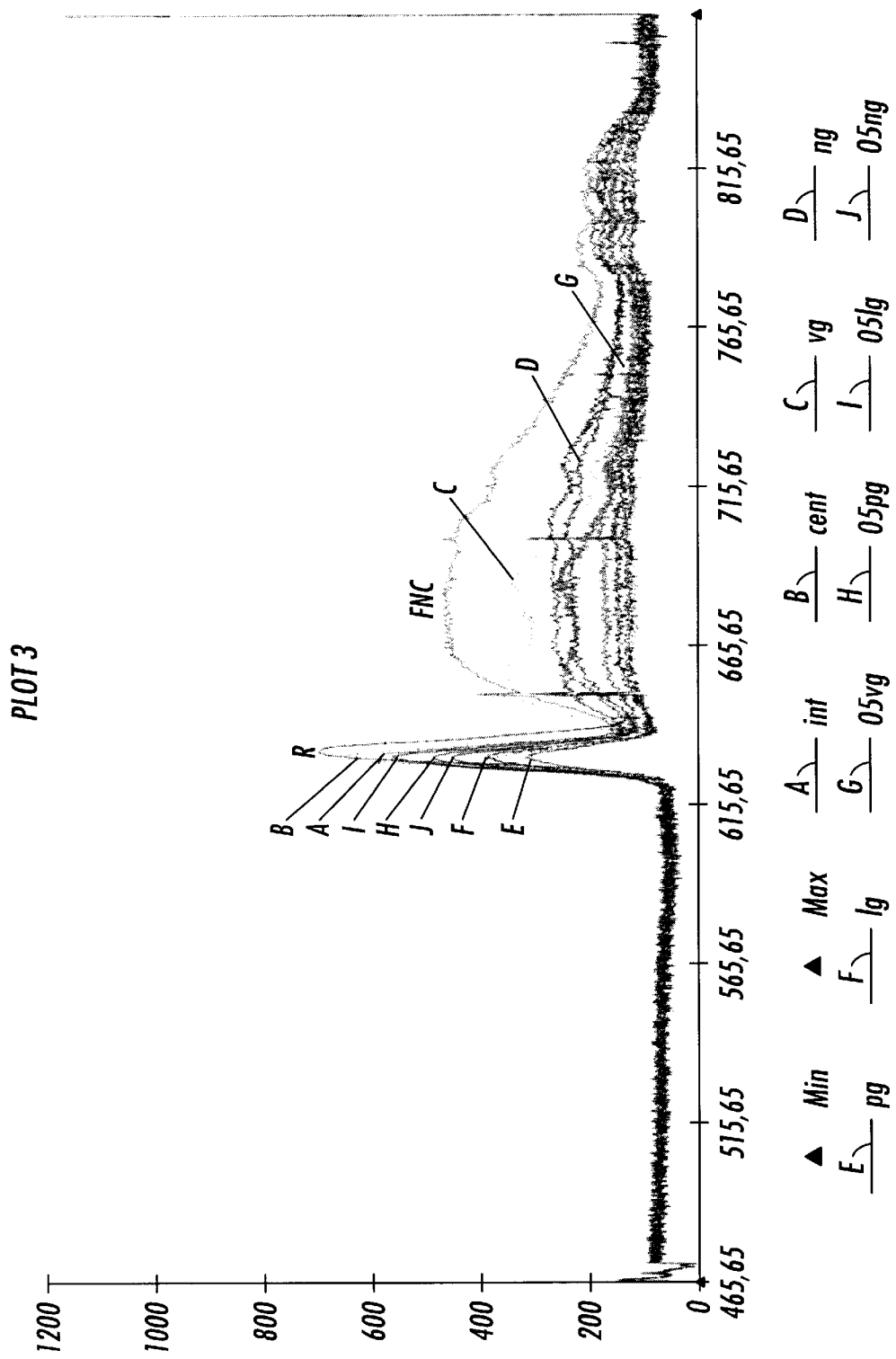

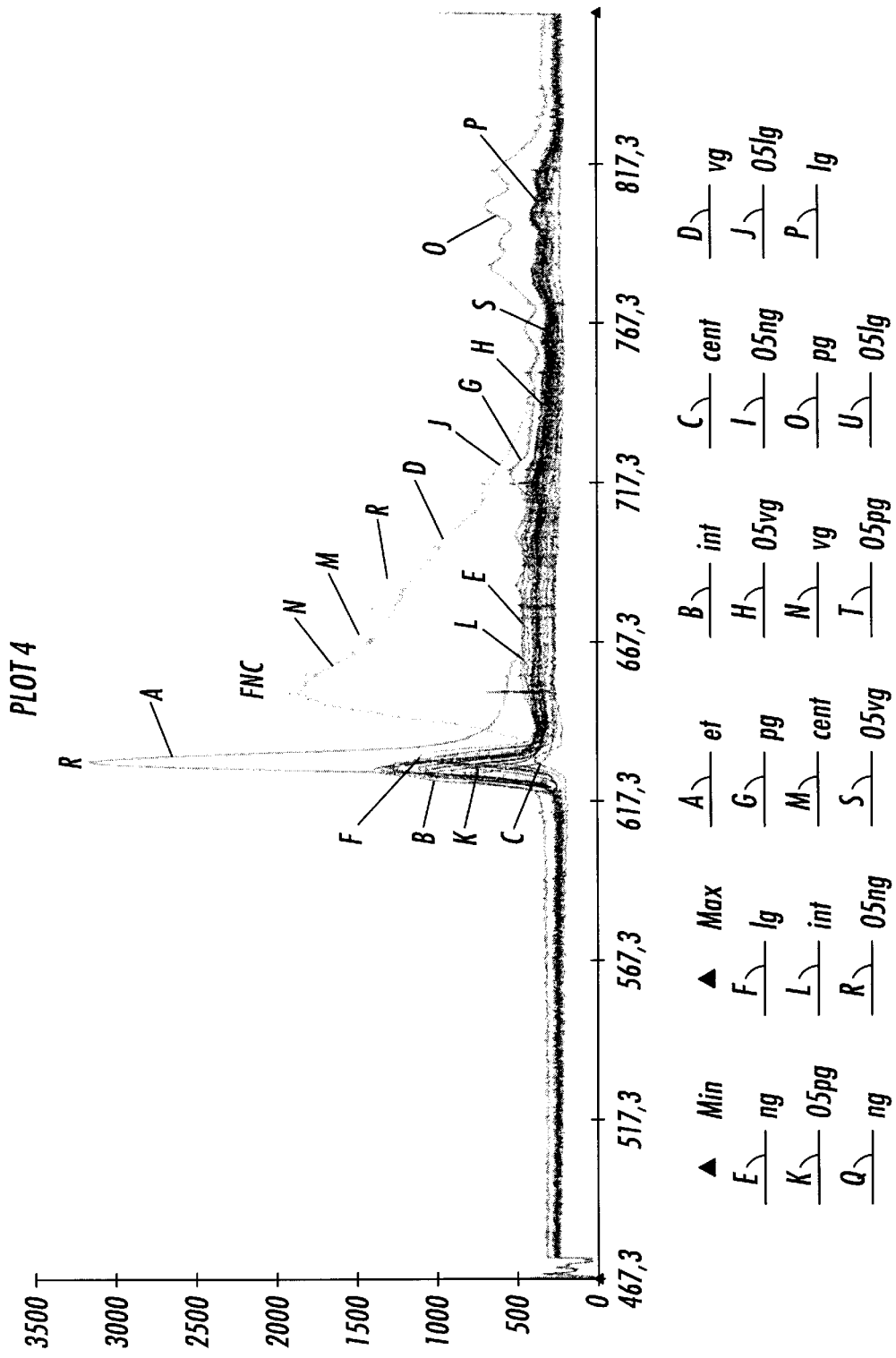

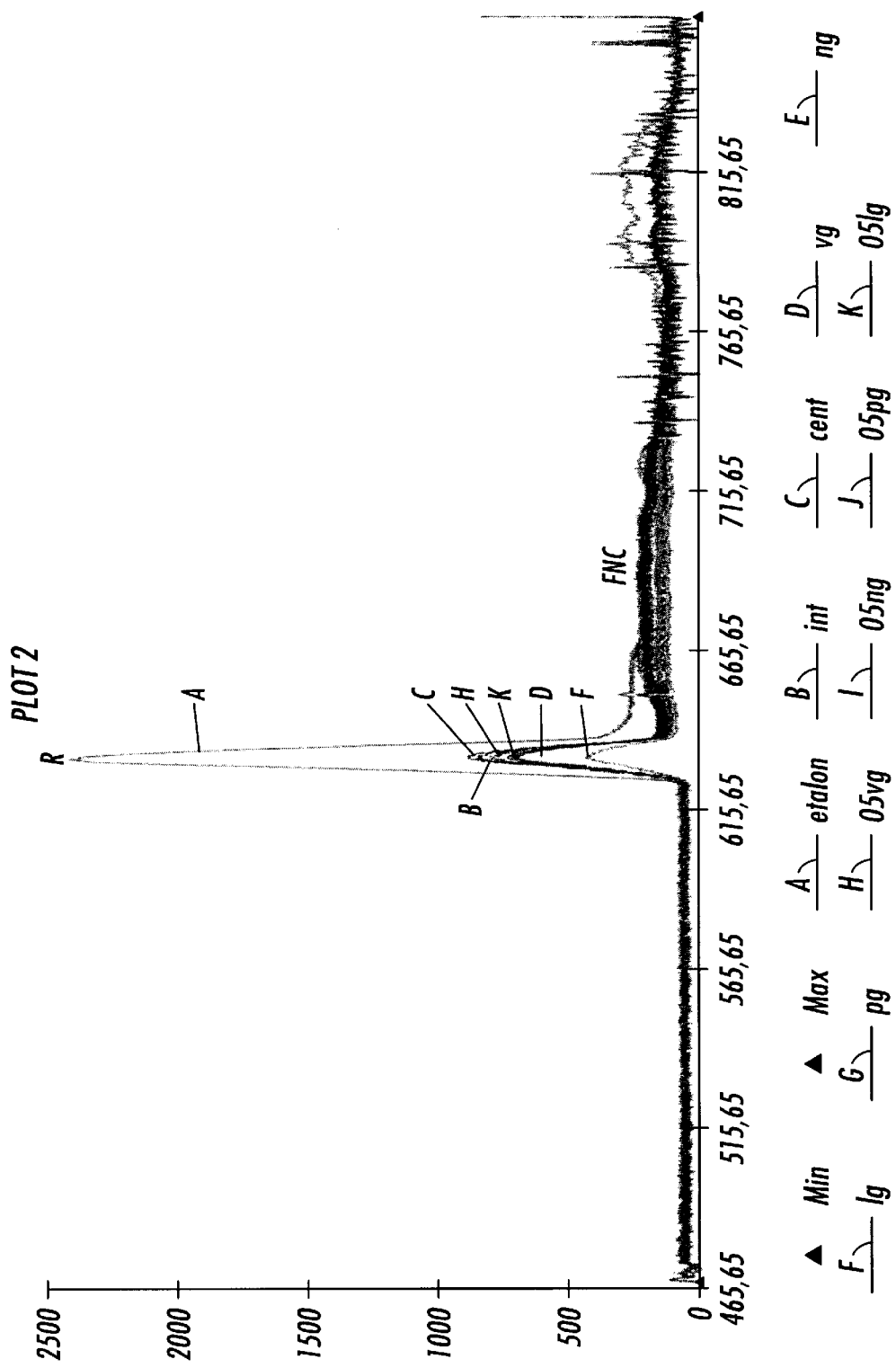

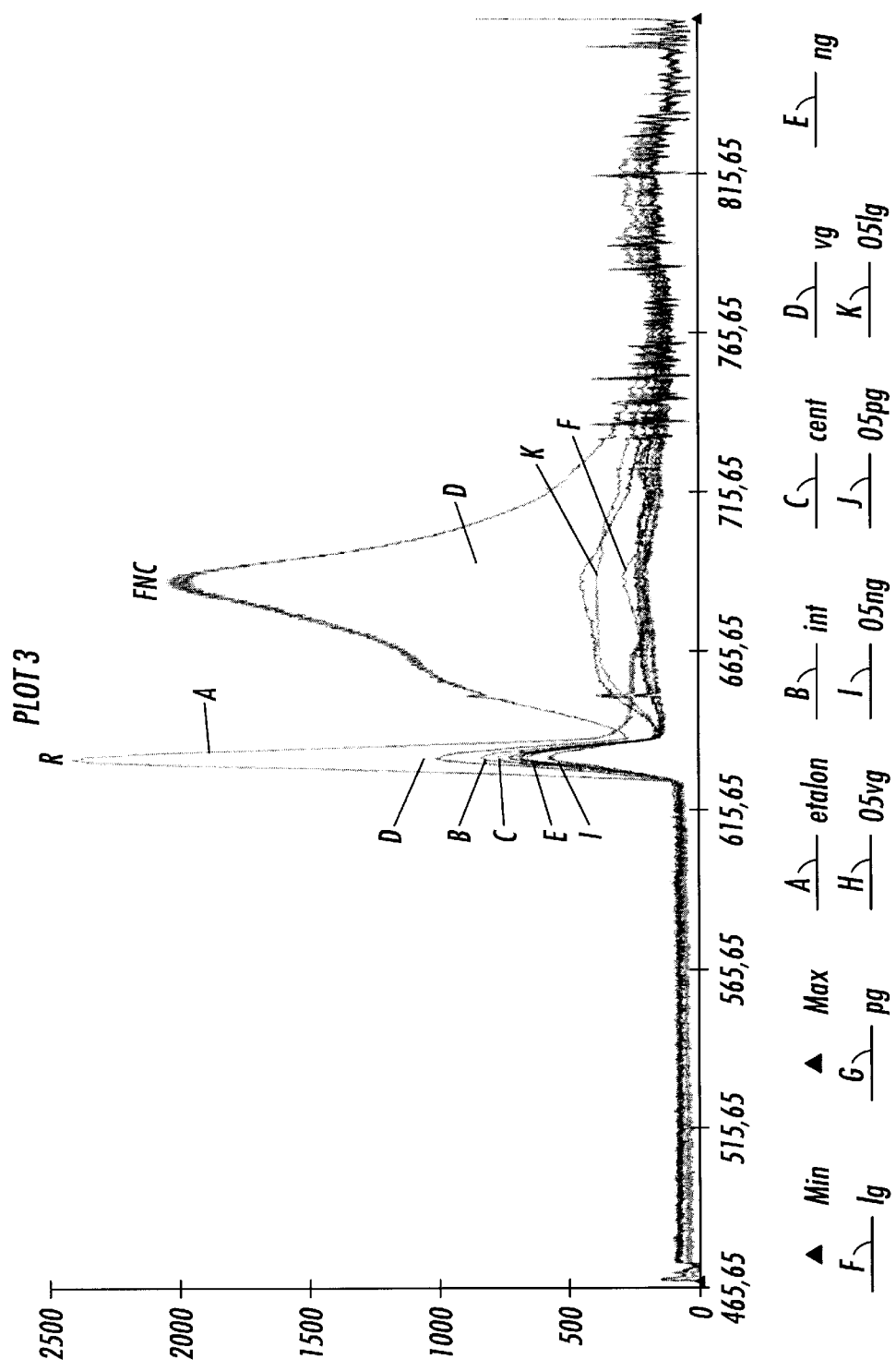

DIAGNOSTIC APPARATUS UTILIZING RADIATION INTERACTION WITH BIOLOGICAL TISSUE

This invention relates to diagnostic apparatus and also to such apparatus which can additionally be used for surgical and therapeutic treatment in the fields of both human and veterinary medicine.

During the last 50 years it has been shown that optical coherent and non-coherent electromagnetic radiation exerts an influence upon biological matter depending on the following parameters, that is, continuity, intermittence, irradiation dose, illumination (power and density), duration and number of doses, structure of the tissue and functional condition of the tissue. The radiation can have no influence on the specific function of the tissue, or it can stimulate the function or inhibit or destroy it by coagulation or ablation.

In 1925 American scientists discovered the phenomenon of so-called "autofluorescence" in which biological tissue fluorescences in the red-orange region of the electromagnetic spectrum after exposure to ultra-violet light. Later tests, made in vivo, have shown that haemotoporphyrin-based preparations, generically known as exoporphyrin, also produce red-orange fluorescence in pathologically changed tissue. Exoporphyrin can thus be used in the diagnosis and treatment of pathological processes and malignant and benign tumours.

JP-A-57-37763 describes a therapeutic device using the medical properties of laser radiation which optimises its parameters according to a change in the reflection coefficient. JP-A-60-83990 describes the medical use of a laser system having fixed irradiation parameters. In two papers respectively entitled "In vivo monitoring of photosensitiser fluorescence during photodynamic therapy" by M. R. Stringer, et al, 104/SPIE Vol. 2371, and "A new method for clinical detection of cancer by rapidly analysing the argon laser induced autofluorescence spectra" by Dong Yang, et al, 104/SPIE Vol. 1616 (1991), the clinical and technological questions of photodynamic therapy and diagnosis are discussed.

The first of those papers describes a method of monitoring the low level fluorescence emitted by the photosensitizing agent protoporphyrin IX during superficial photodynamic therapy of skin carcinomas using 630 nm illumination. A fibre optic probe samples the light field which is filtered and recorded by an optical spectrum analyzer. The technique is minimally invasive and can proceed concurrently with light dosimetry measurement.

In the second paper, a diagnostic system consisting of an argon laser and an optical multichannel analyzer is described. With a special processing program, acquisition of the spectral signal and analysis of the specific index $I_s/I$ are performed simultaneously in real time by a microcomputer where $I_s$ and $I$ are the intensities of the fluorescence in intact and pathological areas which are registered during the stabilization of the laser radiation. The system can be used not only for individual spectral measurements of separate points but for continuous $I_s/I$ scanning of an entire suspicious area as well.

At the basement of the concept evolved in the present invention lie new physical guides of optical radiation interaction with biological tissues as well as modern approach to the development of treatment-diagnostical systems implementing these guides.

In the process of light interaction with biologically active elements of tissue, along with the processes of transmission, reflection, dispersion and absorption, takes place conversion of optical radiation with modification of parameters and characteristics of the probing beam. Some part of the incident optical radiation can be converted in faint, but sufficient for registration, stimulated optical emission. The energy of photon or that of light wave can also be converted into nonstationary acoustic and thermal fields. Although the efficiency of such conversion can be negligibly small and although the part of the converted energy is essentially smaller, than the part of the reflected energy, still the information signals originating therewith can be successfully registered and analysed.

Depending on external conditions (wavelength of the probing radiation, power, modulation frequency, pulse width, pulse energy etc), proportion between signal intensities in every channel of energy dissipation (optical, acoustic, thermal etc) can be different. Accordingly, the registered signals, received by the said channels, can give all-round information of the biological object, characterizing functional, physiological and pathological changes in bio-tissues, because these changes are accompanied by structural, functional and metabolic transformations.

Amplitude, frequency and temporal characteristics of these signals and their variations involve the most important information of vital functions of intact, pathologically transformed bio-tissues, in particular, lesions, injuries, inflammation processes etc. Analysing these signals, it is possible to judge the structure, the functioning, the area of a lesion, to judge metabolic, functionally-biochemical transformations in tissues as well as choice of the method of treatment and its efficiency.

The phenomenon of incident, optical radiation non-linear conversion in biologically active elements of bio-tissue inducing optical, acoustic and thermal secondary radiations and fields (signals) was called by us—Photon-Wave Non-linear Conversion, or in short, PNC-process.

Diagnostics, based on indication and analysis of these processes was called PNC-diagnostics.

The PNC signals received from a biological object, when the latter is irradiated with an optical beam, essentially depend on the object's normal or pathological state. specifically, pathological transformations in tissues are accompanied by modifications of optical characteristics of tissues refraction, dispersion, transmission coefficients, etc), invoking modifications of PC—parameters. This being so, analysing characteristics of the stimulated optical radiation of PNC-signals, originating in the process of irradiation of a bio-object with an optical beam of a given wavelength and power, separately or in combination with the signal, reflected from tissue (R-signal), it is possible to analyse processes of cell-tissue activity, cell-breathing, albumen synthesis, enzyme activity, oxygenation, microcirculation, plastical and neo-plastical processes. Thus, PNC-diagnostics covers all the range of energetical, biochemical and morpho-functional transformations in tissues, organs, in the organism as a whole being in normal or pathological state Concurrently with diagnostics,basing on the feedback principles, it is possible to effect the probing light process of treatment and to control rehabilitation processes.

From a first aspect, the present invention consists in diagnostic apparatus comprising:

(a) a source of probing electromagnetic radiation;

(b) means for transmitting the output from the probing radiation source to biological tissue to be tested;

(c) means for detecting probing radiation reflected from the tissue and stimulated radiation resulting from excitation of the tissue by the probing radiation;

(d) processing means responsive to the reflected and stimulated radiation to produce a signal for diagnosis of the condition of the tissue; and (e) means for regulating the intensity of the probing radiation including a feedback circuit for controlling the regulating means and responsive to the detected intensity of the reflected and stimulated radiation.

The processing means may include means for adjusting the ratio of the reflected probing radiation to the stimulated radiation such as a selective spectral attenuator. The processing means may also include a monochromator for processing the reflected and stimulated radiation.

Preferably, the apparatus includes means for surgically or therapeutically treating the biological tissue.

In an embodiment of the invention, a calibrator for the apparatus is provided, the calibrator including a reflective surface or a surface imitating the optical characteristics of biological tissue, to which surface the probing radiation can be directed in order to produce a standardised signal in response to the reflected and stimulated radiation. A plurality of members may be provided which can be interchangeably fitted to the calibrator, each having a surface imitating the optical characteristics of the biological tissue in a different condition.

Additionally or alternatively, a beam area calibrator for calibrating the area of the probing radiation beam, and a calibrator-reper including a plurality of sources of radiation of predetermined wavelengths may be provided.

From a second aspect, the present invention consists in a method of utilising the apparatus as defined above comprising diagnosing the condition of the biological tissue, surgically and/or therapeutically treating the tissue, and repeating the diagnosis and treatment until the tissue is diagnosed as normal.

The invention provides diagnostic apparatus and a method of calibration thereof both during production and clinical use. The apparatus may use the information-gathering and medicinal properties of coherent or non-coherent light from the visible or non-visible parts of the spectrum for the diagnosis and treatment of a large number of diseases with inflammatory, dystrophic and oncological etiology. It comprises a specialised programmed product and database of pathological processes and operates using the feedback principle in real time.

The apparatus of the invention can be used to measure the reflection and absorption of the fluorescence spectrum in real time. This gives information about blood supply, metabolism, cellular proliferation of intact, inflammatory, dystrophic or oncological tissue and the progress of photodynamic therapy.

The invention will now be described by way of example with reference to the accompanying drawings, in which.

Figure 16A:
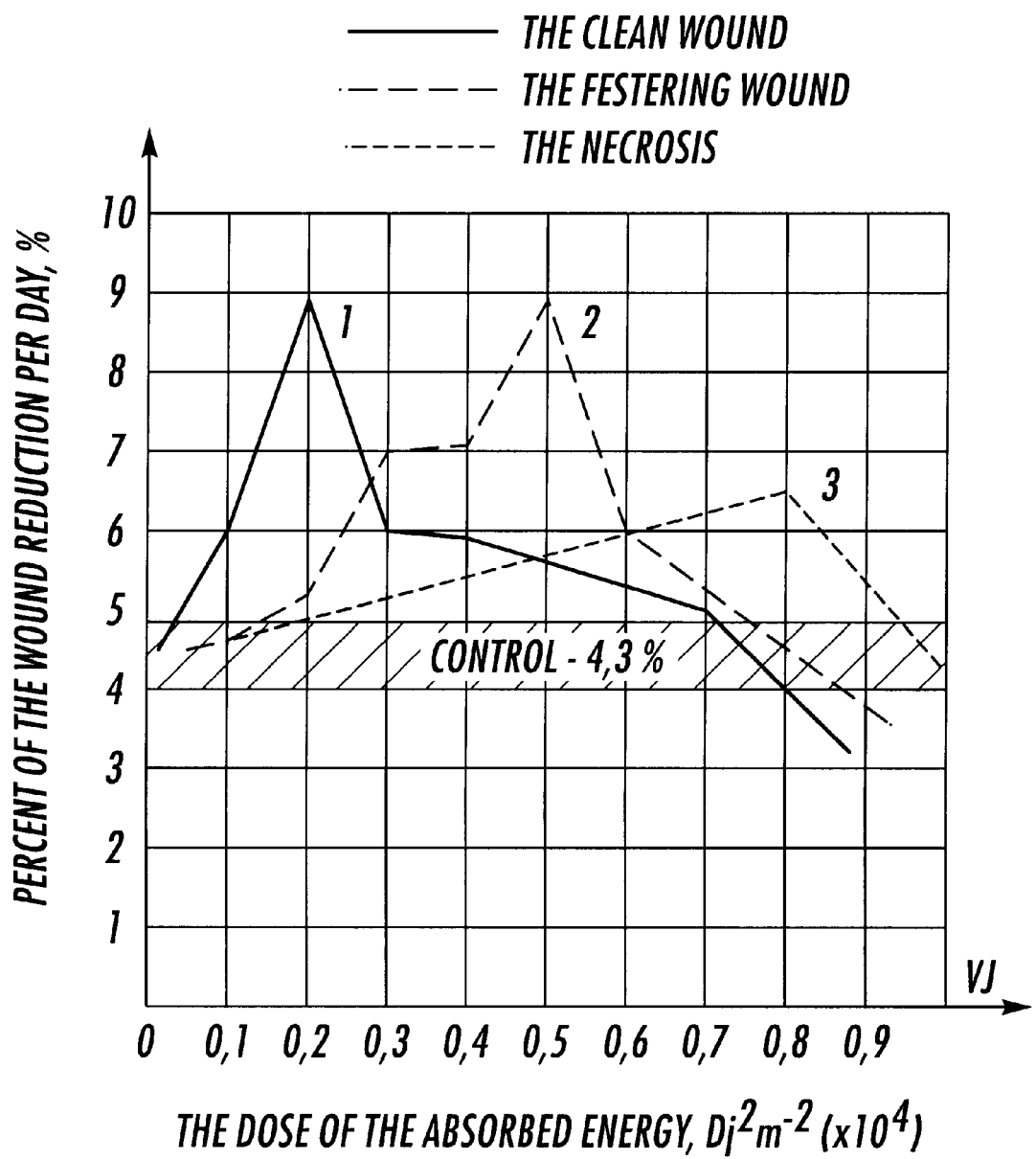
Figure 16B:
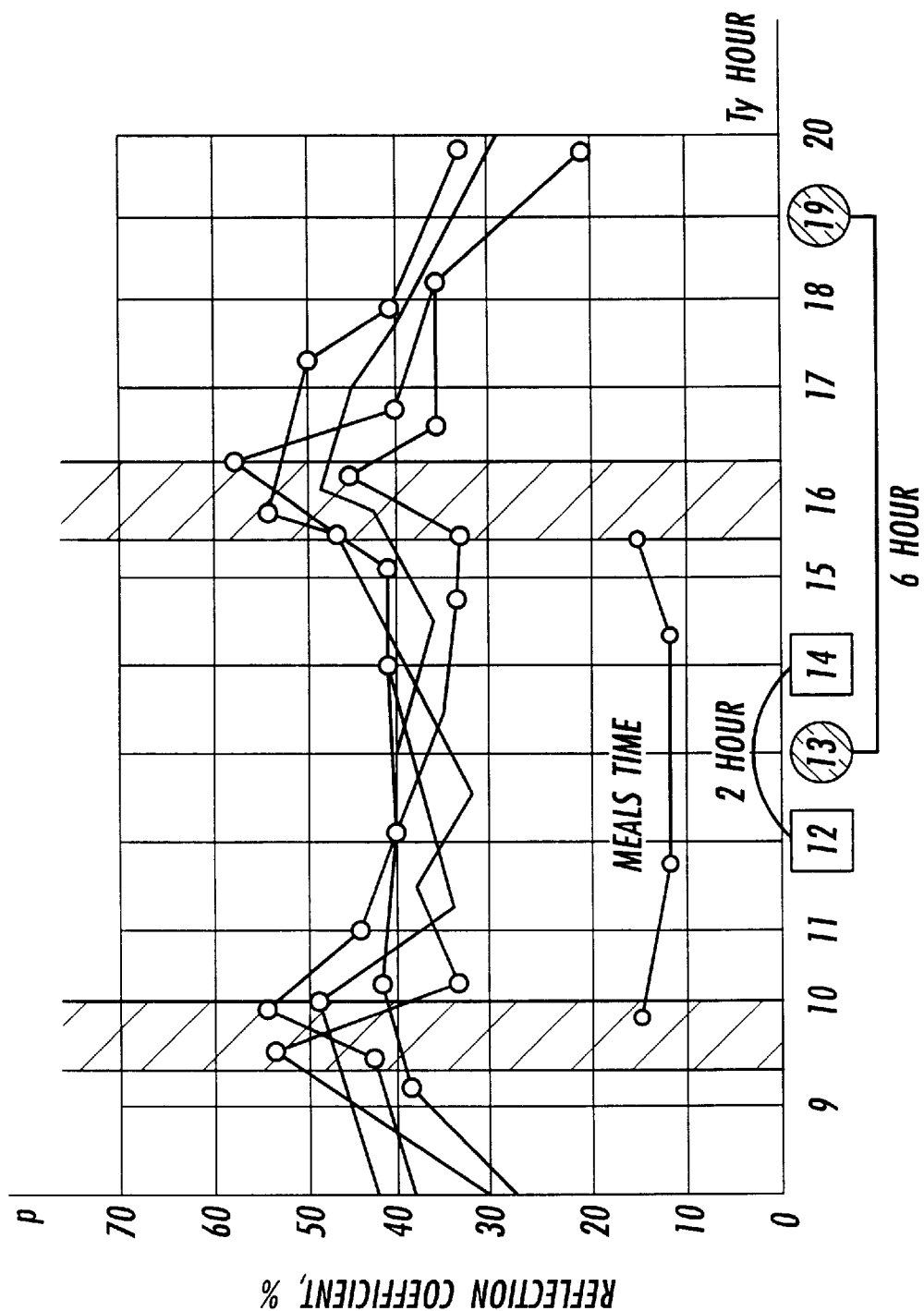

FIGS. 15g to 15m demonstrate spectral distributions for the reflected (R) and stimulated (PNC) signals in the process of treating of oncological patients;

FIG. 16a is a graph of daily percentage wound reduction against absorbed energy dose;

FIG. 16b is a graph of percentage reflection coefficient against time; and

Figure 16C:
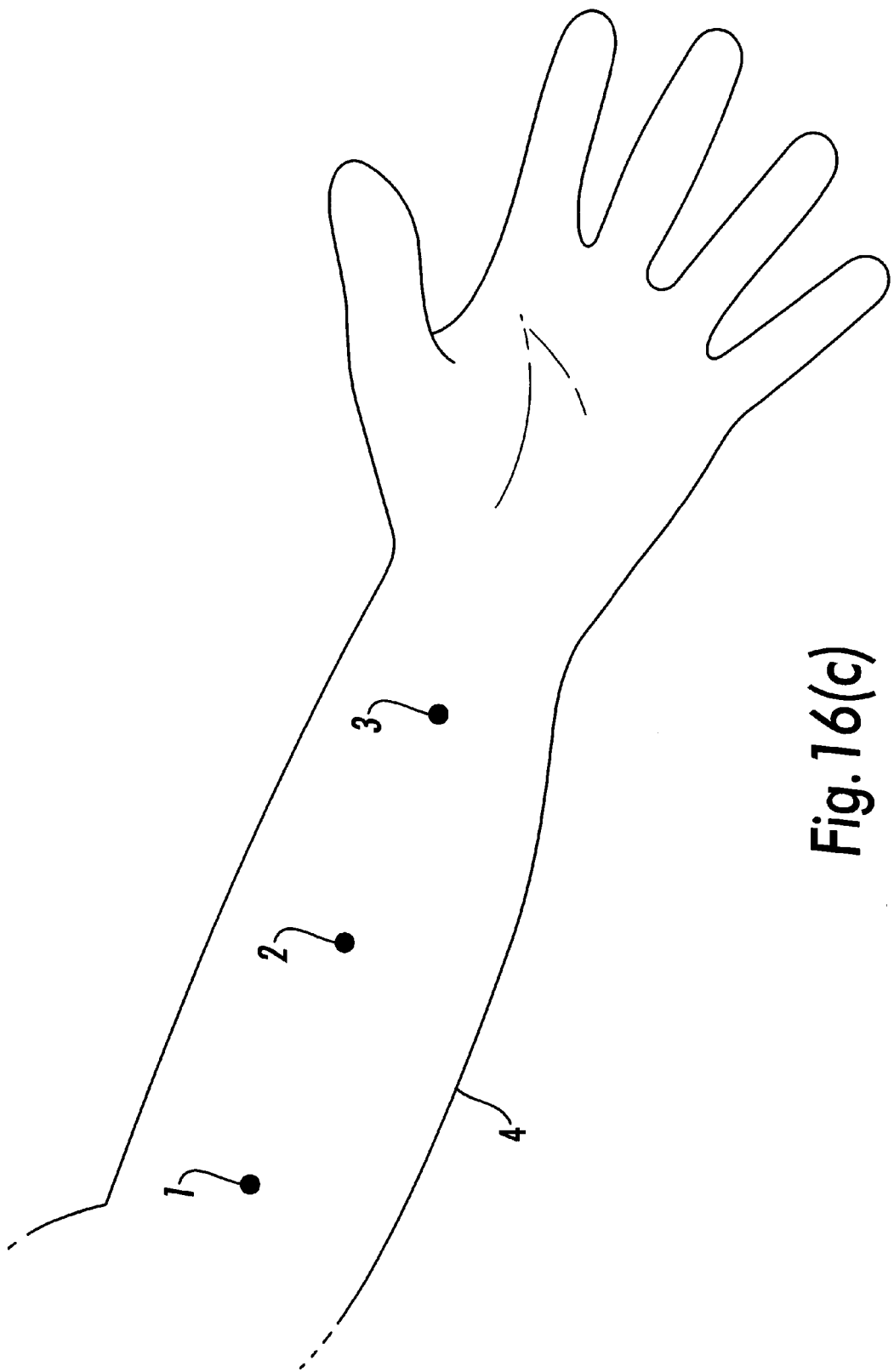

FIG. 16c is a view of a human hand showing where the measurements for FIGS. 16a and 16b were taken.

Figure 17A:
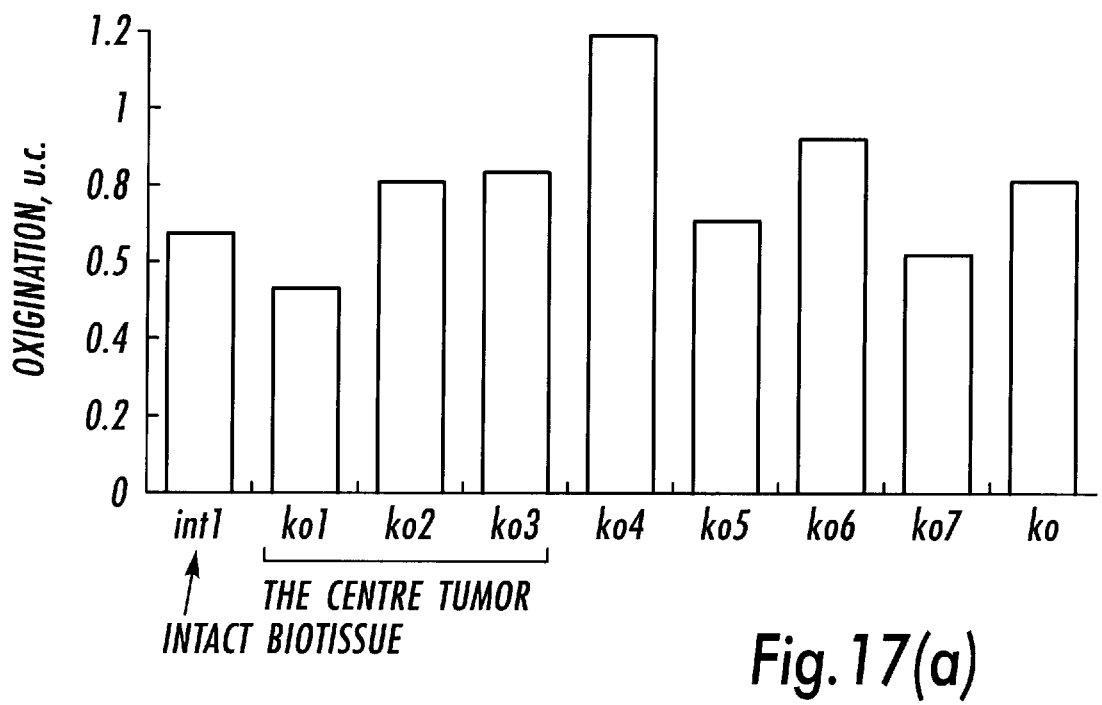
Figure 17B:
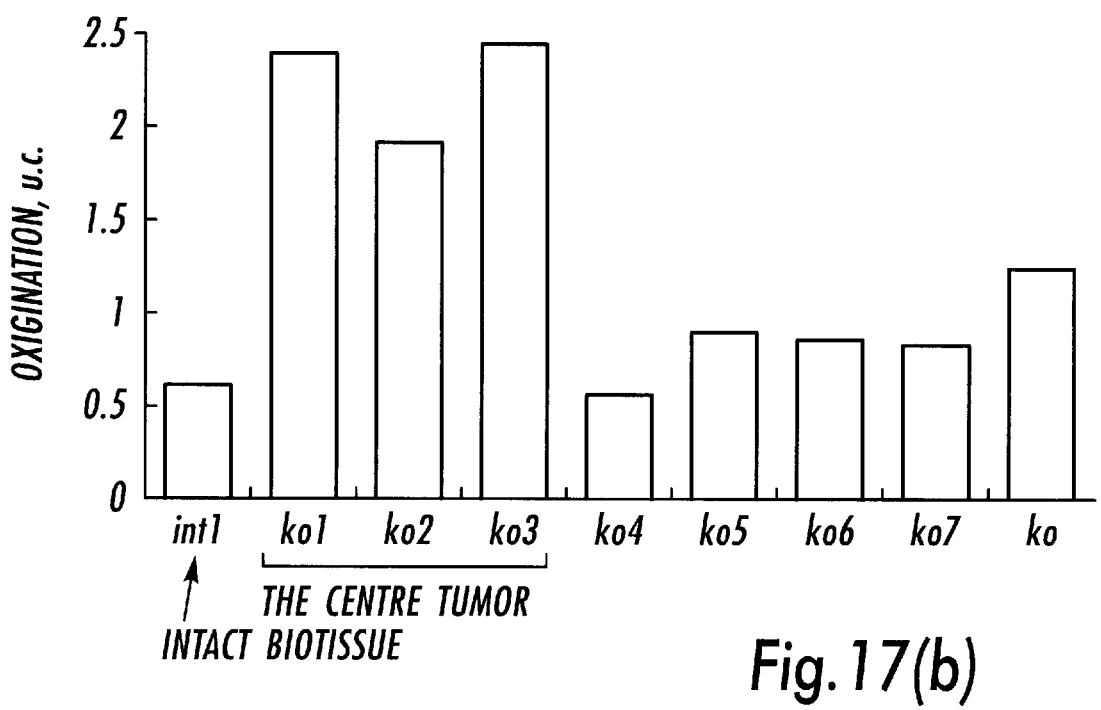
Figure 17C:
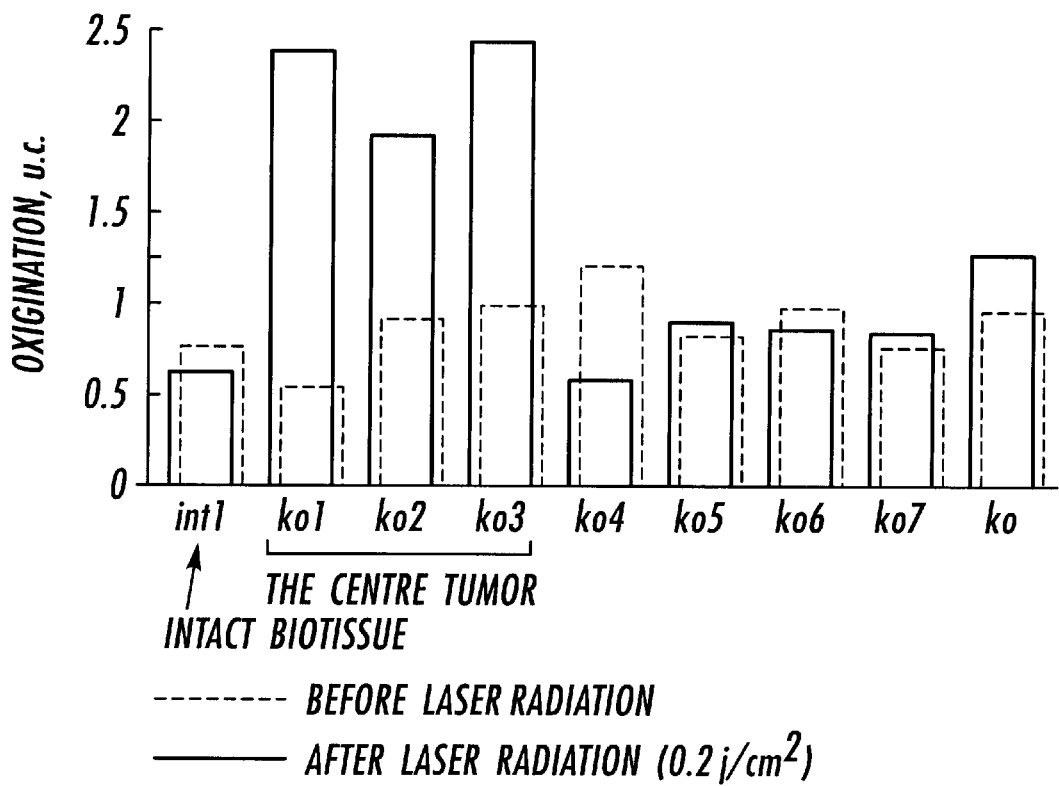
Figure 18A:
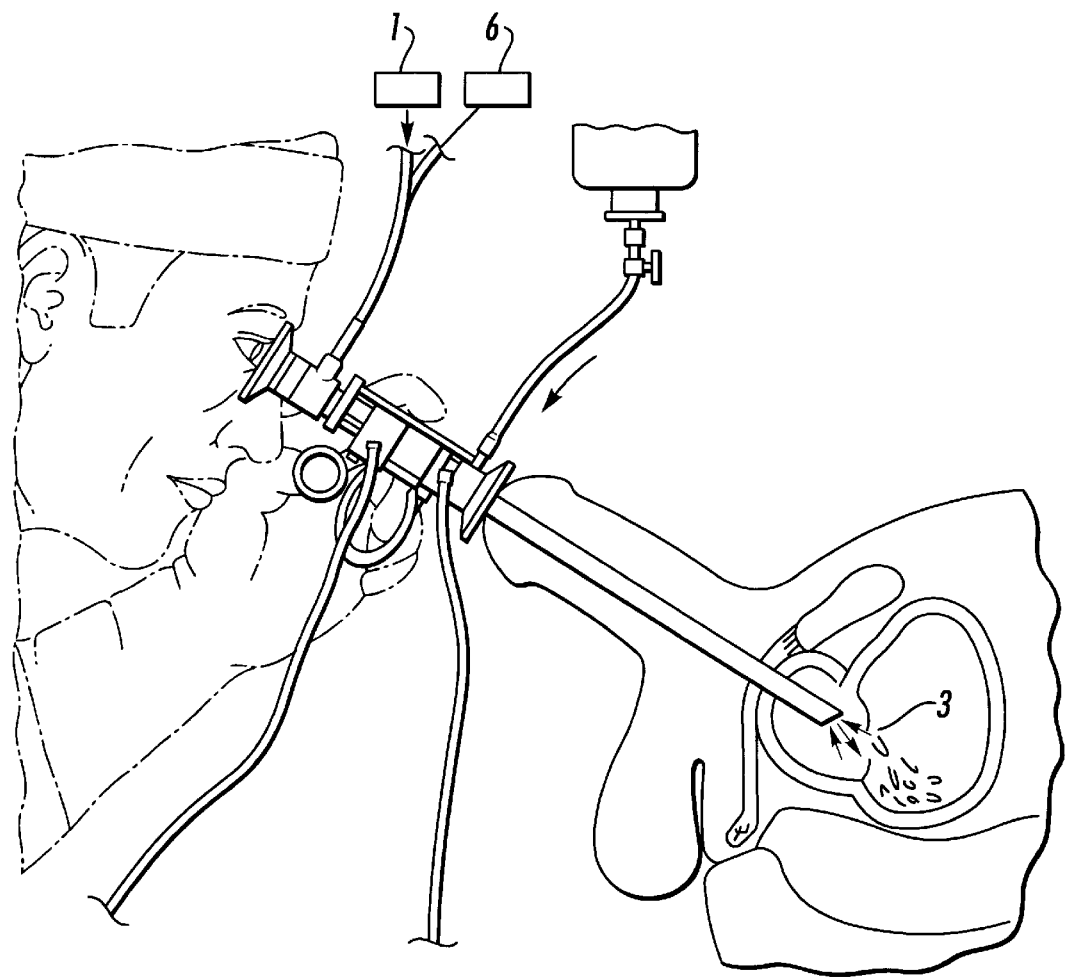
Figure 18B:
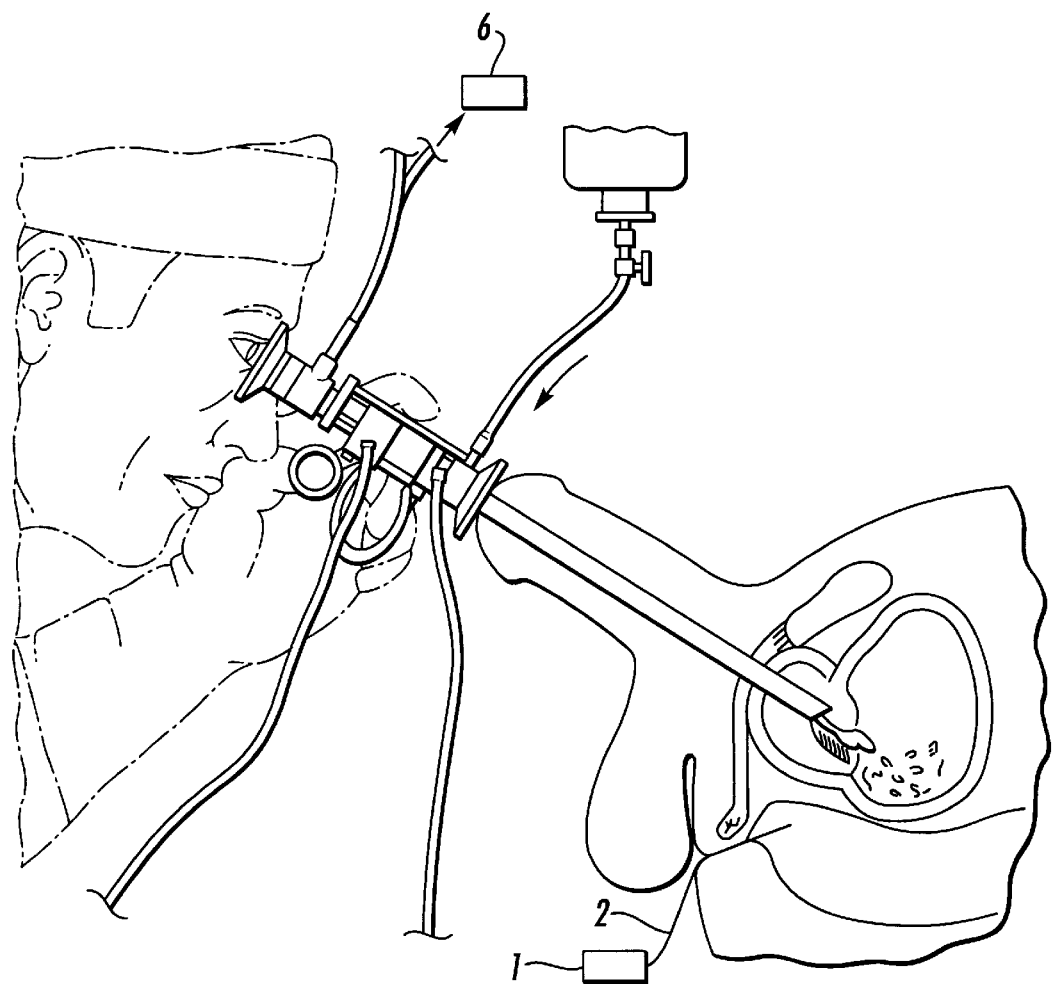

FIGS. 17a to 17c are graphs of optical indices in patients with various pathological processes; and FIGS. 18a and 18b are partially sectional views of prostate treatment using the apparatus of the invention.

Figure 1A:
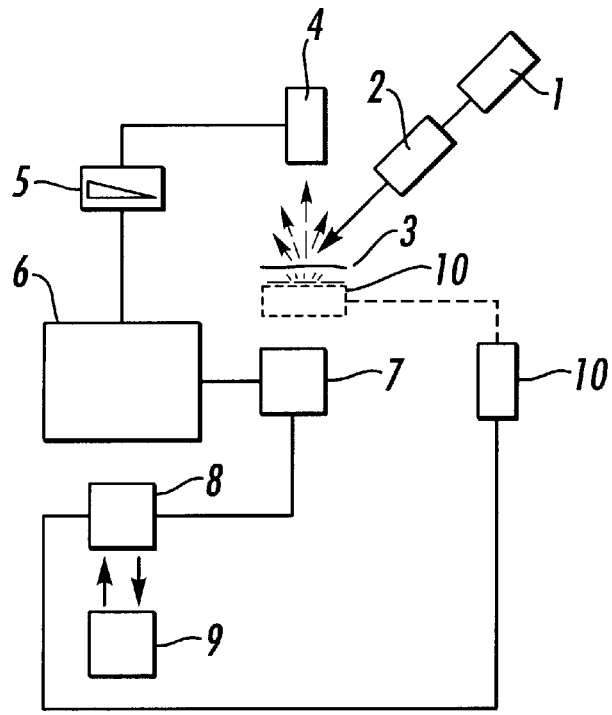
FIGS. 1a to 1c are schematic block diagrams respectively illustrating three embodiments of diagnostic apparatus according to the invention.

FIG. 1a shows apparatus for the examination of intact or healthy and pathological or diseased tissue, including a probing radiation source 1 which in this example comprises a laser. A probing radiation transmission device 2 transmits probing radiation from the source 1 to a biological tissue surface 3 in or on a human or animal body. Due to effective excitation the tissue 3 not only reflects incident probing radiation but also emits stimulated non-balanced radiation. A radiation transmission device 4 transmits both reflected and stimulated radiation to a selective spectral attenuator 5, which is able to change smoothly the absolute and relative intensities of the reflected and stimulated radiations. The light output from the spectral attenuator is supplied to a monochromator 6 having a dispersive optical element and optical ruler and thence to a signal processing device 7, used for signal regulation, amplification, mathematical processing and programming. The signal processing device 7 controls a visual display device 8 such as the monitor of a PC which is loaded with software 9 and displays an image of the area of the biological tissue under examination. The apparatus also includes a calibrator 10 to which the probing radiation can alternatively be transmitted.

Figure 1B:
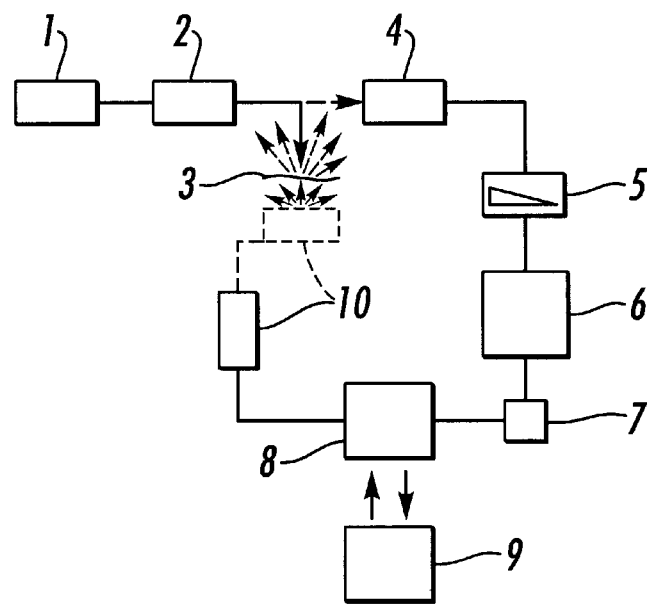
Figure 1C:
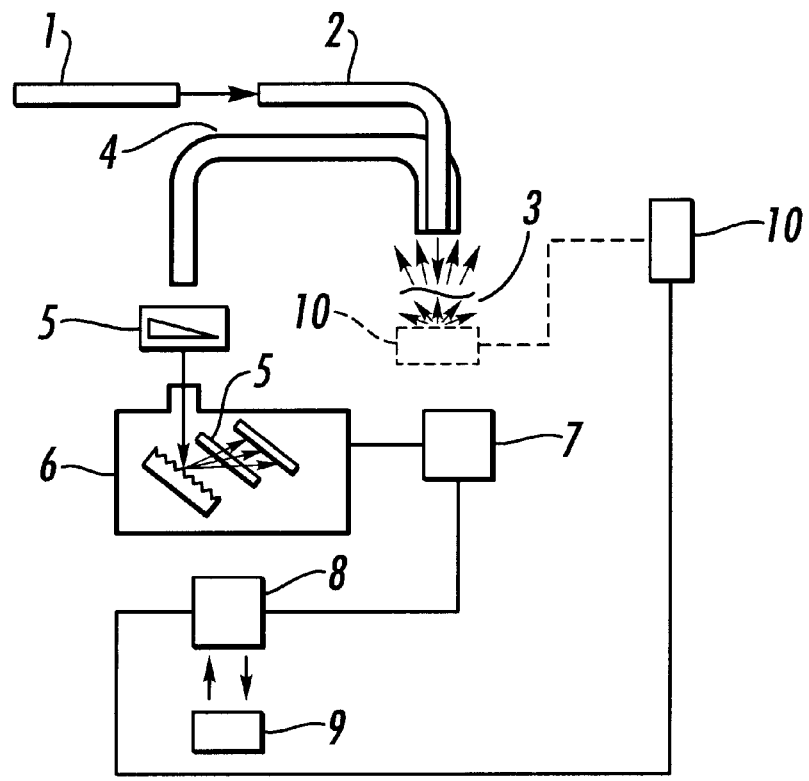

FIG. 1b shows a second embodiment of the apparatus in which the probing reflected and stimulated radiation beams are directed along a common path by means of a reflective device. FIG. 1c shows a third embodiment in which the transmission devices 2,4 for probing and reflected radiation respectively comprise different optical fibres in a multicored fibre optic cable, as will be described below with reference to FIG. 4c.

Figure 2:
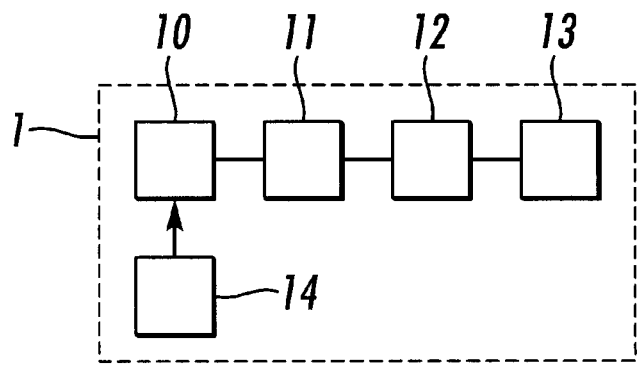
FIG. 2 is a block diagram of the probing light source used in FIGS. 1a to 1c.

FIG. 2 shows in greater detail one of various probing radiation sources which is based around a laser 10. The coherent light emitted by the laser passes through a selective spectral element 11 such as an optical prism or diffraction grating which can if necessary divide radiation of a wide bandwidth into a number of discrete spectral components. A selection device 12 which may comprise a set of light filters selects the discrete spectral components of the light. Thus the wavelength(s) of the probing radiation can be adjusted between 0.3 and 25 μm, in order to obtain information from different depths in the biological tissue, to which the different wavelengths can penetrate. The selection device 12 also controls the intensity and physical location of the discrete components. Subsequently it is necessary to combine the separate radiation components in a wavelength mixer 13 which may comprise mirrors, plane-parallel-plates, lenses and other optical elements, before passing the radiation through a rating device 14.

Alternatively, the probing radiation source 1 may comprise a non-coherent light source such as a high pressure gas discharge lamp instead of the laser 10a.

Figure 3A:
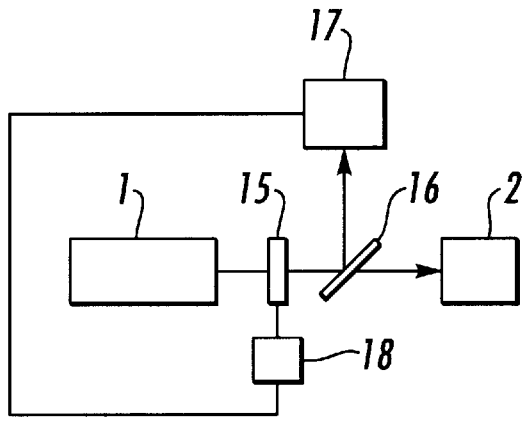
FIGS. 3a to 3c are block diagrams showing alternative feedback circuits for use with the invention.

As shown in FIG. 3a, a polarizer 15 for smoothly regulating the radiation intensity is located at the output of the radiation source 1 on its optical axis. A plane-parallel-plate optical divider 16 directs a proportion, for example from 0.5% to 5%, of the probing radiation to a sensor 17 located outside the optical axis. A drive for rotating the polarizer 15 about its optical axis is controlled by a regulating device 18 which monitors the radiation sensor 17. The optical divider 16, sensor 17 and regulating device 18 constitute a feedback or reverse connection circuit for the automatic control of the intensity of the probing radiation.

Figure 3B:
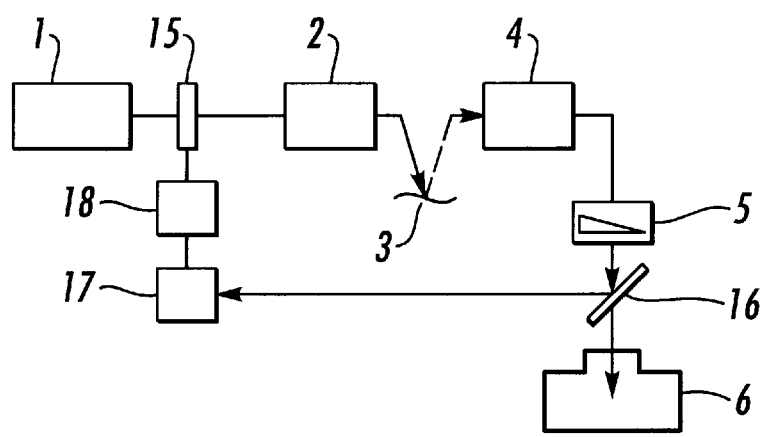

An alternative feedback circuit is shown in FIG. 3b in which the optical divider 16 is located between the selective attenuator 5 and the monochromator 6. Thus the radiation sensor 17 senses the reflected and stimulated radiation instead of the probing radiation. The polarizer 15 can therefore be controlled by the regulating device 18 to vary the intensity of the probing radiation in order to adjust the ratio of the reflected probing to stimulated radiation between limits of 1:1 and 20:1.

Figure 3C:
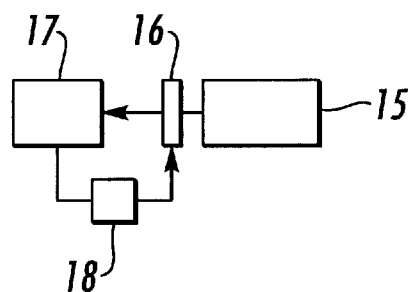

A further alternative feedback circuit is shown in FIG. 3c in which the optical divider 16 forms a partial mirror at the rear of the coherent resonator of the radiation source 1. The transparency of the mirror and, hence, the proportion of the radiation transmitted therethrough, is controlled by the regulating device 18 depending on the radiation sensor 17 which monitors this radiation, in order to adjust the intensity of the probing radiation emitted from the front end of the source 1.

Any of the above feedback arrangements may comprise a fast, stepped, coarse adjustment circuit and a smooth precision tuning circuit. In addition, means for manually adjusting the probing radiation may be provided.

Figure 4A:
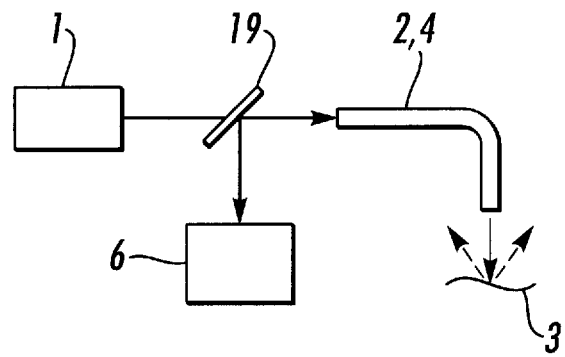
FIGS. 4a to 4c are block diagrams showing alternative radiation transmission devices which can be used with the invention.

FIG. 4a shows an optical fibre 2,4 which constitutes both transmission devices 2,4 for probing and reflected radiation respectively. A selective optical divider 19, located in front of the optical fibre, is coated so as to admit the probing radiation into the optical fibre 2,4 but to re-reflect the reflected and stimulated radiation towards the monochromator 6.

Figure 4B:
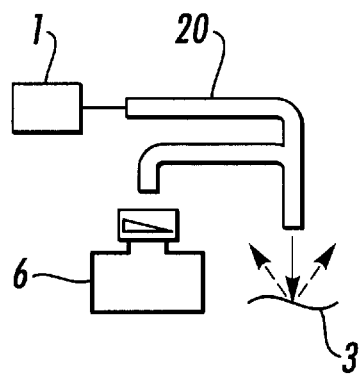

Alternatively, a tapped optical fibre 20, shown in FIG. 4b, can be used, a first branch of which transmits the probing radiation from the source 1 and a second branch of which transmits the reflected and stimulated radiation back from the biological tissue 3.

Figure 4C:
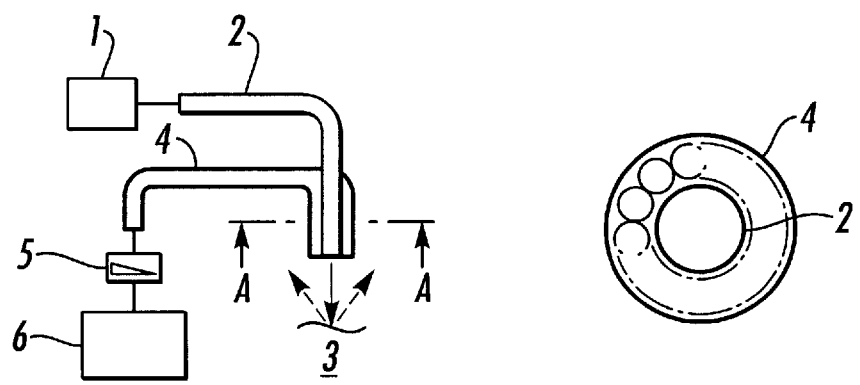

FIG. 4c shows further alternative radiation transmission devices 2,4 comprising at least ten optical fibres in a multicored fibre optic cable. Whilst the figure shows a central fibre 2 transmitting the probing radiation to the tissue 3 and outer fibres 4 transmitting the reflected and stimulated radiation to the spectral attenuator 5, in practice the selection of the different fibres is not ordered and is made at random.

Figure 5:
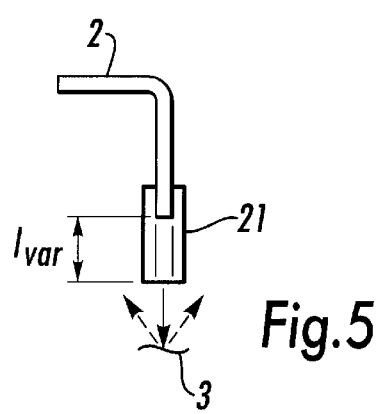
FIG. 5 shows a device for regulating the distance between the end of a light transmitter as shown in FIGS. 4a to 4c and tissue.

FIG. 5 shows a distance regulating device 21 formed as a sleeve which can be fitted to the distal end of any of the optical fibre devices shown in FIGS. 4a to 4c. This device is used to adjust the distance $\lambda_{var}$ between the distal end of the fibre and the biological tissue 3, in order to ensure that the maximum intensity of the reflected and stimulated radiation is received.

Figure 6:
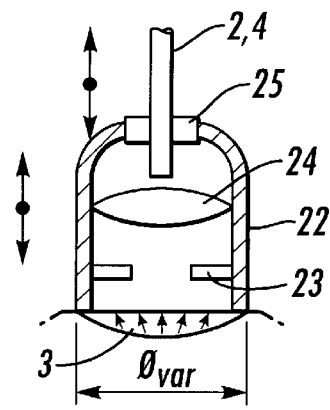
FIG. 6 is a schematic sectional view of an optical nozzle for a light transmitter as shown in FIGS. 4a to 4c.

Instead of the distance regulating device 21, as shown in FIG. 6 an optical nozzle 22 can be fitted to the distal end of the optical fibre 2,4. The nozzle comprises a light-tight hollow cylinder and has a collar 25 which can be attached to the optical fibre at different positions therealong. The diameter $\phi_{var}$ of the nozzle 22 is selected to correspond to the area of tissue intended to be illuminated and the length of the nozzle is at least three times its diameter. A focusing device 24 for focusing the reflected radiation and a regulating diaphragm 23 are mounted inside the optical nozzle 22. The internal wall of the nozzle are capable of transforming the indicatrix of the directed ("mirror") component of the reflected radiation into diffusive radiation. The distal end of the optical nozzle, which contacts the tissue 3, may be cut at an angle of 50° to 85° to the geometrical axis of the nozzle.

The selective spectral attenuator 5 functions by selectively smoothly weakening the intensities of the reflected and/or stimulated radiation by a factor of 20. The attenuator comprises a spectral filter formed as an optical wedge which can be moved angularly and reciprocally relative to the optical axes of the incident reflected and stimulated radiation. The transparency coefficient of the optical wedge for reflected probing radiation can vary from 0.01% to 100% depending on the thickness of the part of wedge on which the radiation impinges, whereas the transparency coefficient for the stimulated radiation has a constant value over the entire wedge. The difference between the transparency coefficients for the reflected and stimulated radiation is due to the difference between the wavelengths of these radiations, and the attenuator 5 thus acts as a narrow stripe optical filter passing light of the probing radiation frequency at a transparency coefficient which is ±0.01% of its maximum, and attenuating all other wavelengths of light by a factor of up to $10^4$.

Alternatively, a selective spectral attenuator can be constructed as, for example, a rotating disk with variable optical attenuation or as some optical element, varying its optical characteristics on an electrical, magnetic or other basis.

The calibrator 10 can be fitted with one of a set of interchangeable plates which may be fluoroplastic. The set includes a reflective plate (calibrator-reflector) which reflects more than 40% of the probing radiation and therefore has an effective reflection coefficient for this radiation $\rho_{eff}$ of 100% defined by $$\rho_{eff} = \frac{\rho_{prob}^{reflect}}{n\rho_{prob}}$$

where n is the transparency coefficient of the reflected probing radiation in the spectral attenuator 5, and $\rho_{prob}^{reflect}$ and $\rho_{prob}$ are the intensities of the reflected and incident probing radiation respectively. In the range of wavelengths of the stimulated radiation, however, the effective reflection coefficient of this plate must not exceed 0.5%.

Another plate in the set has optical characteristics imitating those of an intact biological tissue. The surface of this plate diffusively disperses light and is coated with an artificial derivative of haematoporphyrin, such as photosense 1,2 or protoporphyrin IX, which fluoresces when illuminated by light having the wavelength of the probing radiation. The reflection coefficient of this plate for such a wavelength is greater than 40%, the effective reflection coefficient lying between 80% and 100%. With respect to light in the wavelength range of the stimulated radiation, this plate has a reflection coefficient between 5% and 100%.

The set of plates also includes one or more plates imitating the optical characteristics of pathological tissue. These plates also have diffusively dispersive surfaces and different concentrations of the coating which is fluorescent when illuminated by the probing radiation. These plates reflect more than 40% of the incident probing radiation and their effective reflection coefficients lie in the ranges 0.5% to 80% for the probing radiation wavelength and above 80% for the stimulated radiation wavelength. A number of such plates may be provided, having different optical characteristics correlated to real pathological states of biological tissue.

It will be appreciated that the apparatus can be calibrated by illuminating the different calibrator plates with the probing radiation and measuring the resulting reflected and stimulated radiation.

Figure 7:
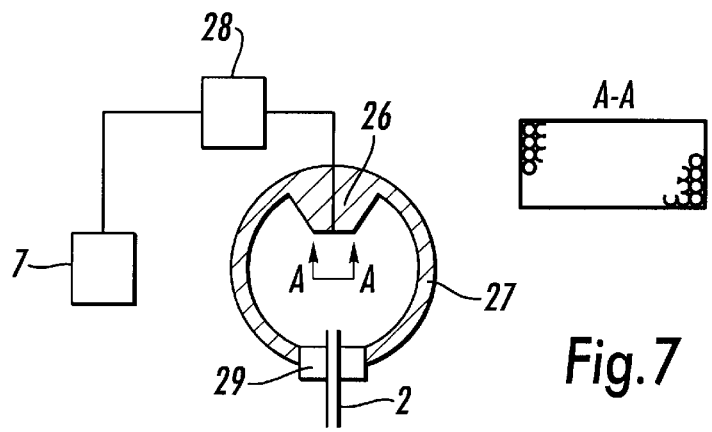
FIG. 7 is a schematic diagram showing a calibrator which can be used with the invention.

FIG. 7 shows an additional calibrator for the area of the beam or pencil of probing radiation incident on the surface of the tissue. A plate 26 is mounted in a chamber 27 which is echoless for the probing radiation. The plate has an array of sensors which can detect the probing radiation and which are arranged in a predetermined geometry. A beam determination device 28 determines the illuminated area of the array and supplies this information to the signal processing device 7. The input orifice of the chamber 27, a fixing device 29 for fixing the distal end of the optical fibre 2 and the plate 26 are all mounted on a common optical axis. The fixing device 29 is operable to move the distal end of the optical fibre smoothly towards and away from the plate 26.

Figure 8A:
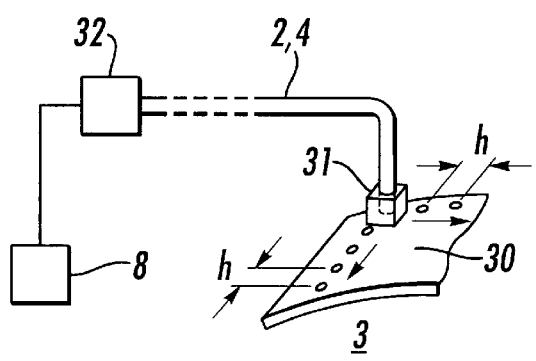
FIGS. 8a to 8c are schematic perspective views of devices for determining the limits of a pathological area of tissue.

An additional calibration device, shown in FIG. 8a, is used to determine the area and limits of the pathological tissue. A carriage 31, to which the distal end of the optical fibre 2 can be attached, is movably mounted on a frame 30 of plastics material. The carriage is capable of moving in discrete steps equal to at least three times the diameter of the probing radiation beam. In this way the scanning and collimated probing radiation is applied to the predicted pathological region and the stimulated radiation is monitored by a video camera having an array of sensors responsive to the stimulated radiation wavelengths. The results are interpreted by a programming device 32 and supplied to the PC 8. The limit of the pathological area of tissue is the isoline along which the radiation received is the same as that obtained using the calibrator plate imitating intact biological tissue.

Figure 8B:
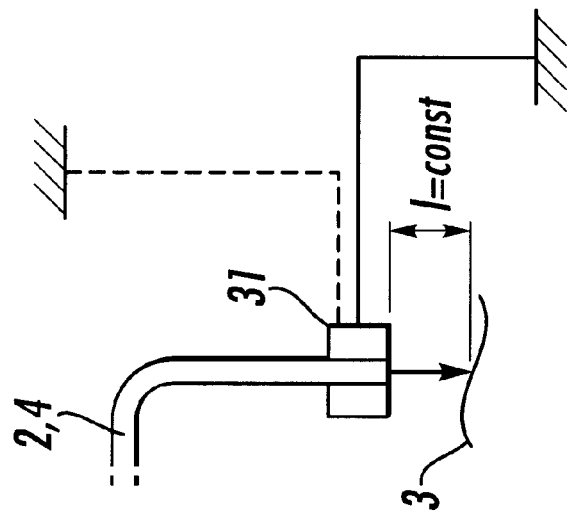
Figure 8B:
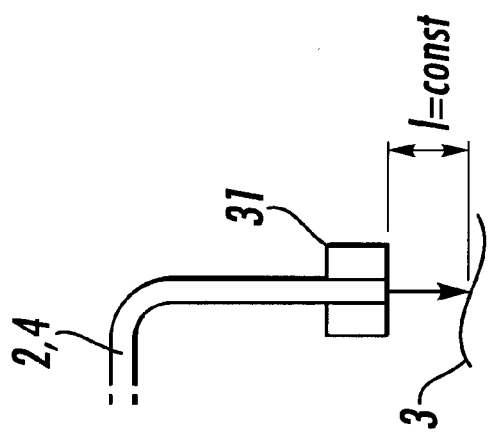
Figure 8B:
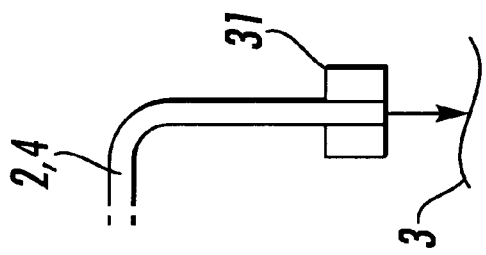
Figure 8B:
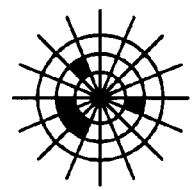
Figure 8B:
Figure 8C:
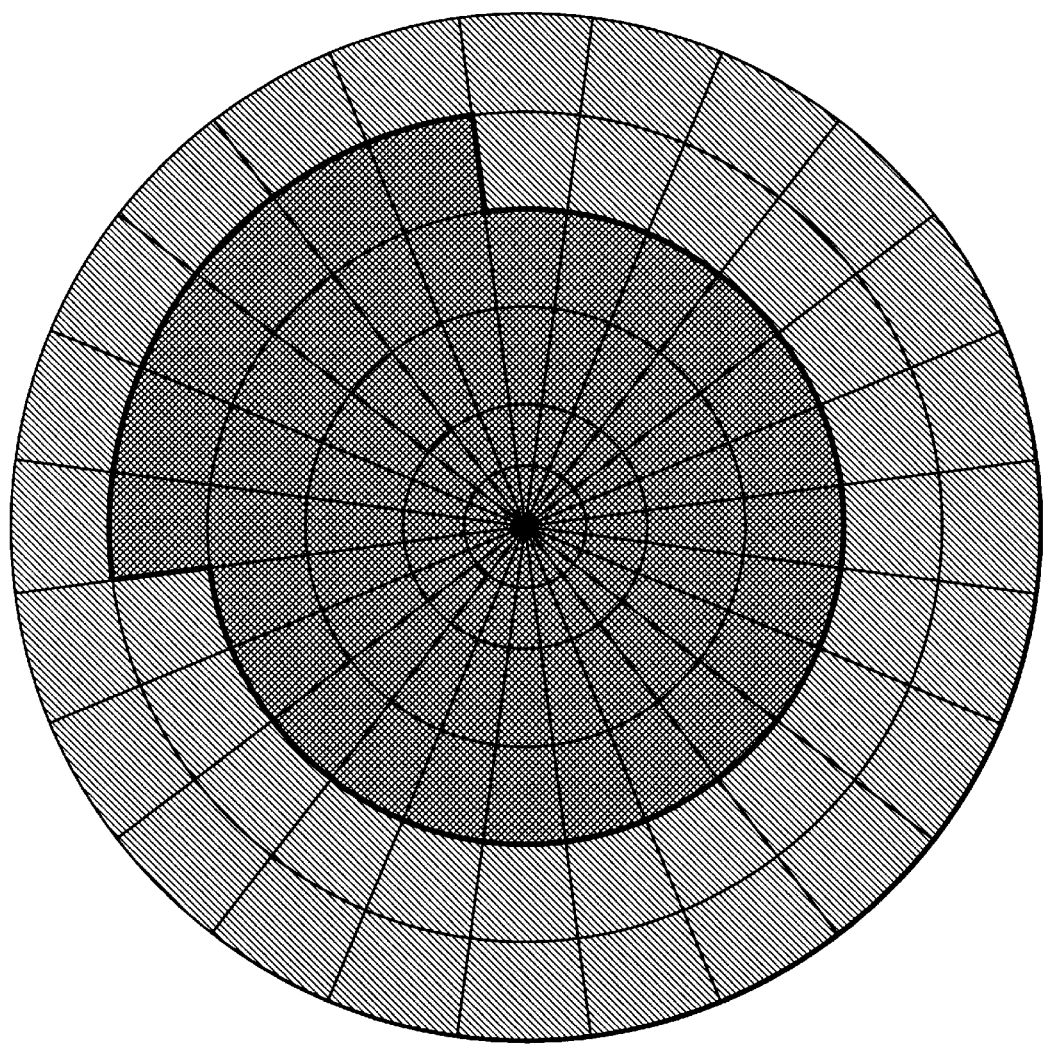
Figure 8C:
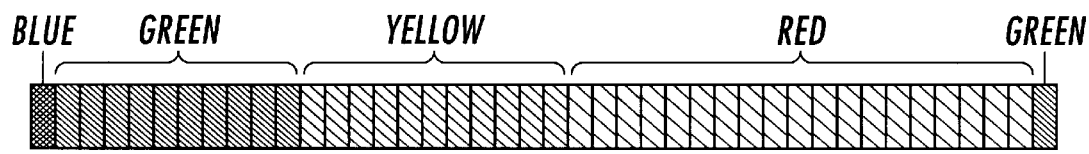

Alternatively, the device depicted in FIG. 8b, is used to define areas and borders of pathological tissue. Device 2, used to transmit the probing radiation signal and device 4,41, used to detect the probing radiation signal, reflected from tissue 3, and to detect a stimulated radiation signal, are all incorporated in assembly unit 31. The unit 31 is designed as a space scanner. The scanning mechanism allows checking signals against discrete pathological spots and/or given areas subjected to diagnostics. Consequently, it is possible to obtain graphical images of lesions with enhanced or depressed activity of cells in comparison with the background of adjacent healthy tissues. Primary and additional colours suggest the state of activity of tissues and cells inside the spots and areas of suspicion, FIG. 8c. the green colour indicates normal process of cell activity, the blue colour—depressed activity and additional colours from blue to red reflect the activity enhancement degree. The cell activity relative index is subjected to AD transformation and special software, basing upon this data, shall diagnose the pathological process activity. Said additional colouration allows the defining of borders and area of the lesion (see left upper corner of FIG. 8c).

The assembly unit 31 can be constructed as a stationary unit of units 2, 4, 41 and is intended for stationary instalment at a given distance from the plane surface of biological tissue to reflect anatomical salient features of the lesion under survey. Such a unit can be used both to detect the state of maxillofacial tissues and tissues of all other parts of the body.

A calibrator-reper of the apparatus comprises two or more calibrated radiation sources with known discrete fixed wavelengths between 0.23 and 25 $\mu$m. An optical connection device connects the calibrator-reper to the distal end of the reflected radiation transmission device 4 and is capable of applying the different fixed radiation wavelengths to the transmission device simultaneously or consecutively.

Figure 9:
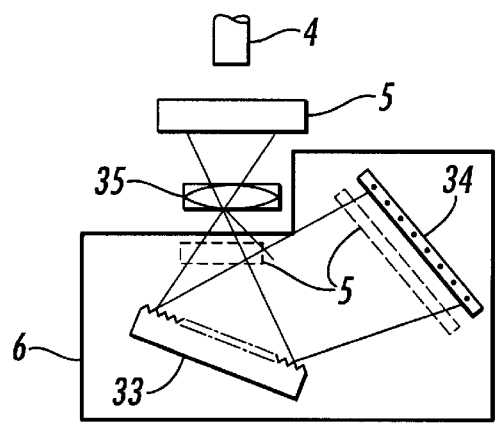
FIG. 9 is a schematic sectional view of a monochromator of the apparatus.

FIG. 9 shows the arrangement of the spectral attenuator 5 and monochromator 6 in more detail. An optical system such as a lensed transfocuser 35 is located either between the attenuator and the monochromator, as shown, or in front of the spectral attenuator 5. The transfocuser includes a focusing element, preferably a segment of a gradan-type lens for focusing the reflected and stimulated radiation, which element is movable along the projected optical axis of the reflected radiation transmission device 4. The transfocuser 35 transmits the reflected and stimulated radiation beams to a dispersive element 33 of the monochromator 6 and is capable of regulating the diameter of these two beams at the surface of the dispersive element. The beams are reflected from the dispersive element 33 to an optical ruler 34 within the monochromator. An additional monitoring device is also provided in the monochromator 6 for detecting spectral components in selected narrow spectral ranges.

Alternatively, spectral attenuator 5 can be placed both before the dispressive element 33 and after it, before the optical ruler 34.

Figure 10:
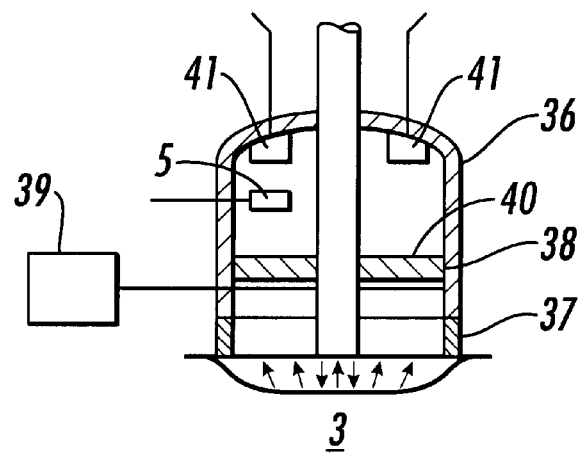
FIG. 10 is a schematic sectional view of an alternative optical nozzle.

FIG. 10 shows an alternative optical nozzle 36 to that shown in FIG. 6. The nozzle 36 is also mounted coaxially on the distal end of the optical fibre 2 and comprises a hollow cylinder, the walls of which are non-fluorescent and have a reflection coefficient greater than 80%. A removable light-tight ring 37 at the distal end of the nozzle is capable of being sterilized. A variable diaphragm 38, mounted in the nozzle 36, is capable of reducing the internal diameter thereof to 80% of its maximum value and is controlled by a programming device 39. The nozzle also contains a diffusely dispersive plate 40 having a transparency coefficient 30%.

The distal end of the optical fibre 2,4 within the nozzle 36 may be contained within an optical screen consisting of a fabric cylinder. The walls of this screen are transparent to optical radiation and are coated with a material which absolutely absorbs the probing and stimulated wavelengths. The nozzle 36 may also contain a gap-polarizer and an optical analyzer mounted in front of the diaphragm 38 and capable of rotating through 360° relative to the optical axis.

The reflected radiation transmission device 4 need not be an optical fibre and may instead be an electrical conductor. Wavelength-selective sensors 41 mounted in the optical nozzle 36 convert the stimulated and reflected radiation into electrical signals. The sensors 41 are shielded from direct incidence of the reflected radiation by the diaphragm 38 and the diffusely dispersive plate 40. The transmission device 4 supplies data from the sensors 41 to the signal processing device 7 via autonomous devices with variable amplification coefficients.

Figure 11:
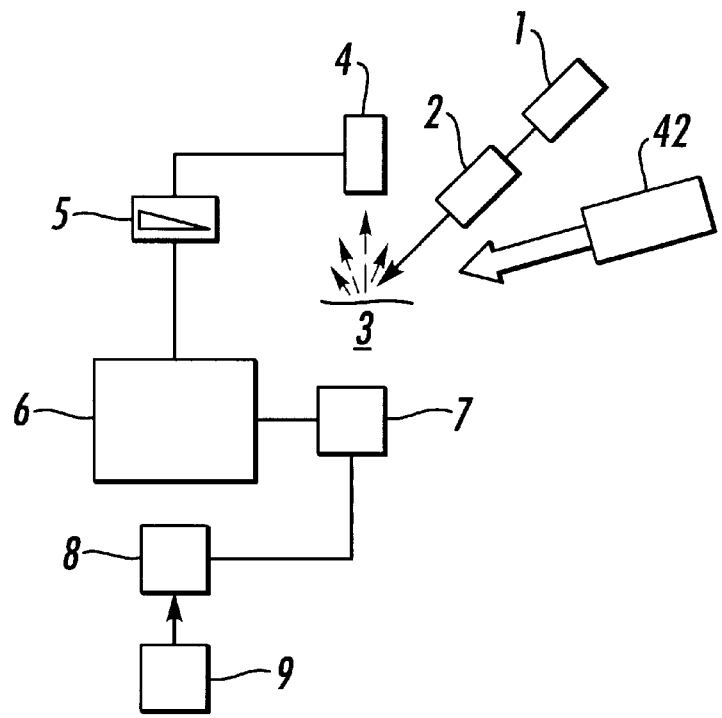
FIG. 11 is a schematic block diagram of a diagnostic apparatus according to a fourth embodiment of the invention.

The fourth version of the invention, incorporating external unit 42 which allows regulation of the stimulated emission intensity upon the tissue 3 under survey is shown in FIG. 11. Specifically, unit 42 can incorporate an optional source of radiation producing beta and/or gamma radiation and/or a source of optical radiation emitting in the waveband 0.2–11 μm and also some cooling unit regulating temperature on the surface or inside the volume of the tissue under survey.

The optical radiation can be directed colinearly backward with respect to the probing one.

Besides that, unit 42 can perform the stimulating radiation intensity regulation basing upon biological, chemical, electrical and magnetic methods or by means of the injection of medications.

Specifically, electromagnetic fields can both increase and decrease the stimulated emission intensity. For example, the electromagnetical bio-tissue molecule ionization leads both to amplitude variations and frequency shifts of the stimulated emission intensity maximum.

Such chemical and biological activating agents as manganese, bismuth, copper, alkali addition to water solutions etc.—not only do they change the stimulated emission intensity, but they also influence relaxation time of biological tissues and specifically they influence the temporal parameters of the fluorescence. The hydrogen ion concentration decrease shall increase the stimulated emission effectiveness.

Modulation and/or variation of amplitude, frequency and temporal (relaxation) parameters of the probing radiation 1 or similar parameters of external units (42) described above allow the gathering of both statistical and dynamical characteristics of bio-tissue under survey and, consequently, the execution of diagnostics of their state.

Figure 12:
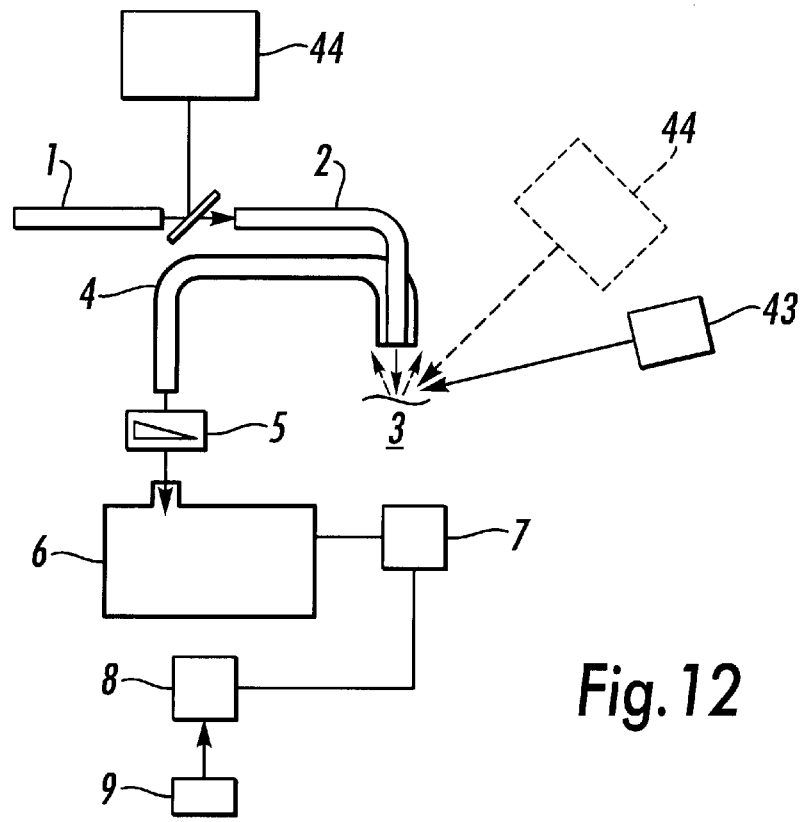
FIG. 12 is a schematic block diagram of a diagnostic and therapeutic apparatus according to a fifth embodiment of the invention.

A fifth embodiment of the invention, shown in FIG. 12, includes the pathological area determination device 43 as described above with reference to FIG. 8, and a surgical and therapeutic device 44. The surgical device 44 uses for example X-rays, optical or laser radiation and is controlled by software and a database depending on the diagnostic data obtained, to carry out dynamic therapy specific to the particular patient.

Specifically, unit 44 can incorporate some source of radioactive emission to effect radiant radiotherapy, units for measuring microcirculation and/or tissue oxygenation with the object of overcoming resistance and controlling radio modifying properties of hypoxical lesion cells.

The tissue oxygenation stimulation unit can be designed either in the form of some optical source radiating in waveband 0.4–11 μm, or in the form of some electromagnetic field source. The tissue oxygenation stimulation intensification also is possible by local means, generating oxygen (or its derivatives) and/or oxygen containing mixtures in lesion area or oxygen to be consumed with breathing inside pressure chamber. Besides that, the unit 44 can be designed in the form of a unit intended for vasodilating injections.

The unit 44 can also incorporate a subunit intended for noncontact measuring of such biological parameters as roughness, turgor, humidity etc. Specifically, it can contain elipticity-meter intended for cosmetology implementation.

Figure 13:
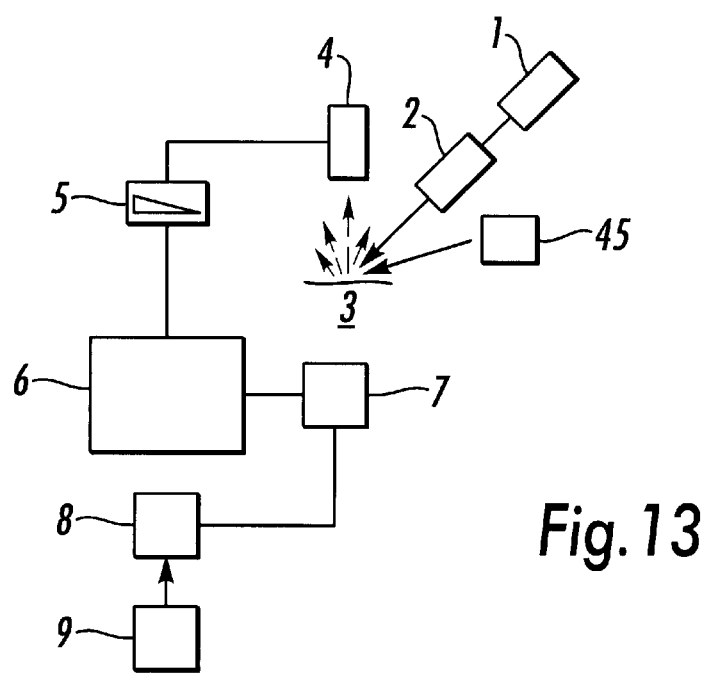
FIG. 13 is a schematic block diagram of a diagnostic and therapeutic apparatus according to a sixth embodiment of the invention.

FIG. 13 shows a sixth embodiment of the invention which includes a photoplethysmograph 45 for measuring microcirculation and/or oxygenation of tissue. The photoplethysmograph may contain a impulse generator, an amplitude modulator and a radiation source connected in series, and a light receiver, a selective amplifier, a rectifier, a low frequency filter and a stripe amplifier also connected in series.

An automatic radiation intensity regulator, connected between the output of the low frequency filter and the input of the amplitude modulator, comprises a differential amplifier, a comparator and an impulse generator. The outputs of the differential amplifier, impulse generator, stripe amplifier and intensity regulator are connected to the inputs of a data output device which produces a photoplethysmogram showing the blood pulse signal, the first derivative of this signal and the zero crossing points of the first derivative. Alternatively, the photoplethysmograph may comprise a capacitative energy accumulator having a charge capacity sensor the energy exposure of which is calibrated within the range 0.001 to 1000 J/cm$^2$. The output from the photoplethysmograph is fed back to control a therapeutic optical irradiation dosimeter.

Figure 14A:
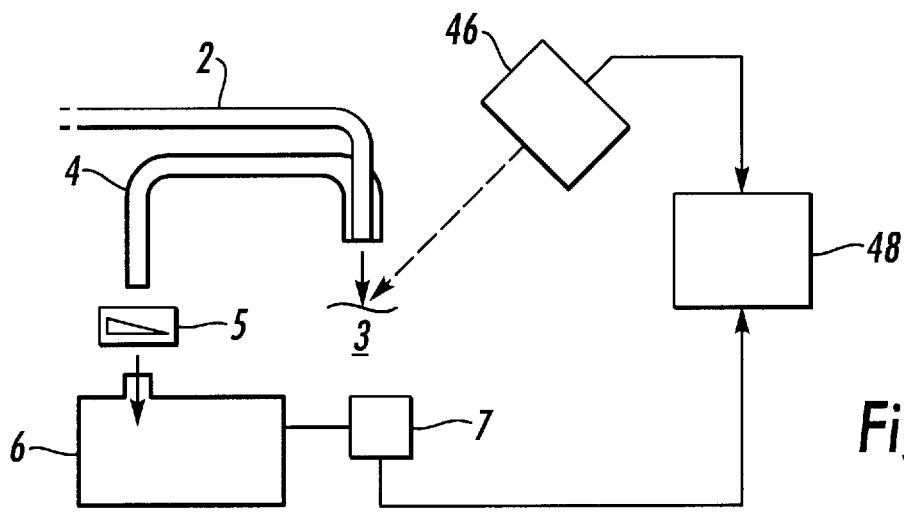
FIGS. 14a to 14c are schematic block diagrams of a diagnostic apparatus according to a seventh embodiment of the invention.

FIG. 14a demonstrates the 7th version of the invention, incorporating unit 46 intended to transmit video images obtained from the tissue under survey 3. This version also incorporates a pathological area detection subunit (FIG. 8); the borders of the lesion are represented on monitor 48 intended for matching two or more images obtained through different methods.

Figure 14B:
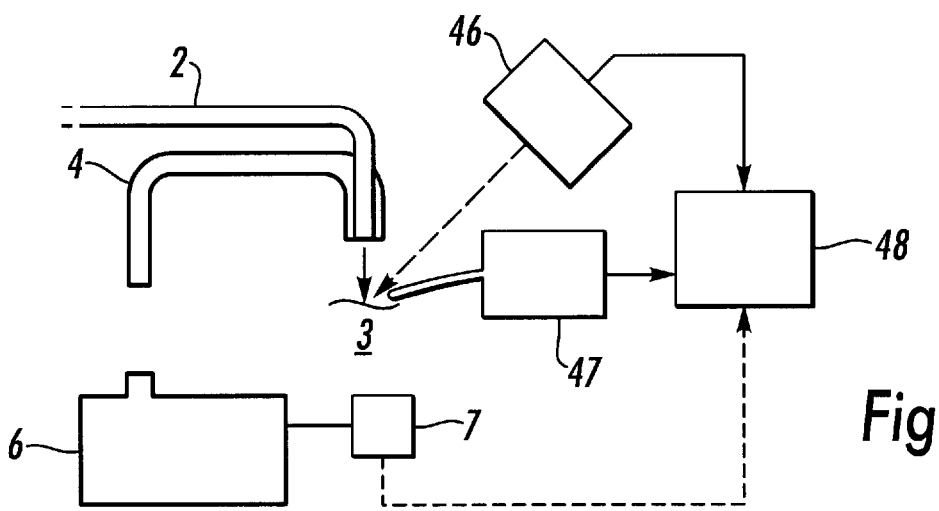

The version also incorporates other means of medical visualization of inner and surface structures of a living body to obtain and match diagnostic images obtained on the base of Roentgen, ultrasonic, magnetic-resonance, thermographic, radio-nuclei and computer-tomographic methods and their complex implementation (FIG. 14b).

The units indicated above allow obtaining preliminary information of the lesion of interest.

Figure 14C:
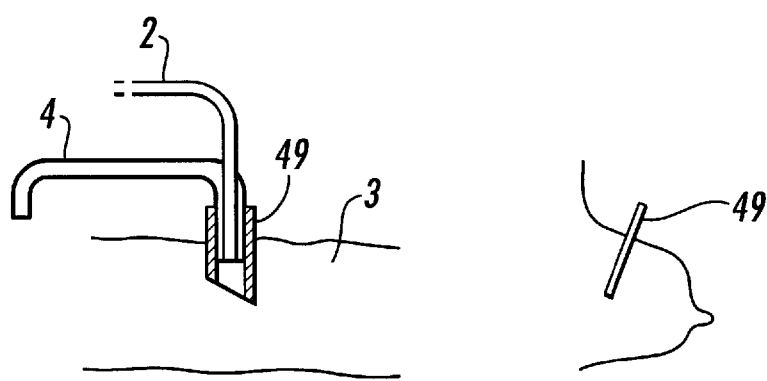

FIG. 14c suggests a version of the invention that can be used in mammography.

The apparatus may also include further surgical or therapeutic devices, for example a copper vapour laser optically filling dyestuff and a non-linear crystal such as LBO. The laser generates light of wavelengths 0.25, 0.29, 0.51, 0.58 μm and in the range 0.6 to 1 μm and is capable of switching between different wavelengths and combinations thereof. The therapeutic radiation may be transferred to the biological tissue via the probing radiation transmission device 2, a plane-parallel-plate, mounted in the optical axis of the transfer device being transparent to the probing radiation and re-reflecting the therapeutic radiation. Alternatively, the surgical and therapeutic devices may have their own radiation transfer devices.

Optimally, the apparatus can incorporate wavelength tunable (0.3–25 μm) radiation source, used both for surgery and therapy, for example—it can be the laser on free electrons.

Methods of using the apparatus of the invention will now be described.

In order to calibrate the apparatus, firstly the scale of wavelengths is calibrated by marking reper points from the calibrator-reper. Next, using the reflective plate of the calibrator 10, the spectral properties of the reflected radiation are determined by collating the displayed signal amplitude and wavelength. The intensities of the probing and stimulated radiation are calibrated using the different plates of the calibrator 10. Finally the probing radiation transmission device 2 is calibrated using the beam are calibrator of FIG. 7.

The calibration process may include the step of adjusting the spectral attenuator 5 until the minimum ratio of the amplitude of the probing radiation $A_{PR}$, incident on the calibrator plate imitating intact biotissue to the maximum amplitude of the spectral components of the stimulated radiation, $A_{SRMax}$ lies between 1 and 20. This ratio is then minimised within the range 1 to 20, by simultaneously monitoring $A_{PR}$ and $A_{SR}$, whilst keeping the power of the incident probing radiation $P_O$ constant for the minimum probing beam area. Next, using calibration plates imitating pathological tissue and maintaining the ratio $A_{PR}$: $A_{SRMax}$ in the above range, the parameter $C_n=K_n/K_{n+1}$ is adjusted, where $$K_n = \frac{A_n - A_R}{A_n + A_R}$$

$A_n$ is the relative optical characteristic of the examined point, with n being an index number of the point, n being equal to 1, 3 or 5 for points lying in the centre of the examined region, on its limit and at a distance 1 to 2 cm from the limit respectively, and n being 2,4 or 6 for points symmetrical to those points. $A_R$ is the relative optical characteristic of the reper point, which is a point lying in an intact region outside a related anatomo-topographical region and asymmetrical thereto. This point is fixed for all measurement stages and is located, for example, on the inner surface of the elbow, the popliteal space or the foot.

Once the apparatus has been calibrated, diagnosis can take place. Typically, the pathological area determination device of FIG. 8 is firstly used, and within the pathological area, inflammatory, dystrophic or oncological activity is measured by comparing the reflection coefficients of the reflected and stimulated radiation with standardised optical parameters in real time. Surgical or other therapeutic treatment can then be carried out and can be varied dynamically by periodically obtaining the optical characteristics and reflection coefficients using the apparatus, and comparing their rate of change with database information.

In adapting the apparatus for real biological tissue the minimal amplitude ratio in the calibrated system of information retrieval of the amplitudes of the reflected to stimulated radiation is brought within the range 1 to 20 by regulating the intensity of the probing radiation. Also, the ratio of the amplitude of stimulated radiation for intact tissue to that for pathological tissue must not be more than 0.15.

To diagnose an inflammatory, dystrophical or oncological condition, a parameter C can be measured where $$C = \frac{A_{SR\ PATHOLOGIC} - A_{RR\ CALIBRATOR}}{A_{SR\ INTACT} - A_{RR\ CALIBRATOR}}$$

$A_{SR\ PATHOLOGIC}$ and $A_{SR\ INTACT}$ are the pear amplitudes of the stimulated radiation from the pathological and intact tissue respectively and $A_{RR\ CALIBRATOR}$ is the pear amplitude of the reflected radiation, the probing radiation having been standardised for all measurements using the reflective plate of the calibrator 10 with the effective reflection coefficient equal to 1. If C is greater than 1 but less than or equal to 1.05, then a pathological process has been detected. The limit of the pathological area is an isoline joining points where $C=0.98\pm0.05$. The degree of the pathological process can also be determined as follows:

| | |
|---|---|
| 0.2 < C < 0.8 | severe |
| 0.8 ± 0.05 < C < 0.9 | moderate |
| C ≥ 0.9 ± 0.05 | slight |

In addition, the comparison between healthy and affected tissue can also be made by a photoplethysmographical method. The constant and variable parts of the photoplethysmographical optical signal are measured at the six points mentioned above with reference to calibration. $C_n$ is then calculated for which a value of $0.96\pm0.05$ corresponds to normal tissue whereas a greater value indicates a pathological process.

In order to find the limit of the pathological area, $C_n$ can be determined for points starting from the predicted centre of this area and spiralling outwards until the standardised optical index reaches an angle between 15° and 360°. In this case, for the determination of $A_n$, values of n of 1,3 and 5 correspond to points starting at the predicted centre and leading outwards to the periphery of the pathological region, and again values of n of 2,4 and 6 correspond to points symmetrical thereto. If the symmetrical region is absent or difficult to measure, then n+1 points are measured in the intact region. Again, the limit of the pathological region is an isoline joining points having an equal predetermined value of $C_n$. With respect to $C_n$, the degree of expression and/or activity of the pathological process can be determined as follows:

| | |
|---|---|
| 1.05 ≤ C ≤ 1.15 | slight |
| 1.2 < C < 2.5 | moderate |
| C > 2.5 | severe |

Figure 15A:
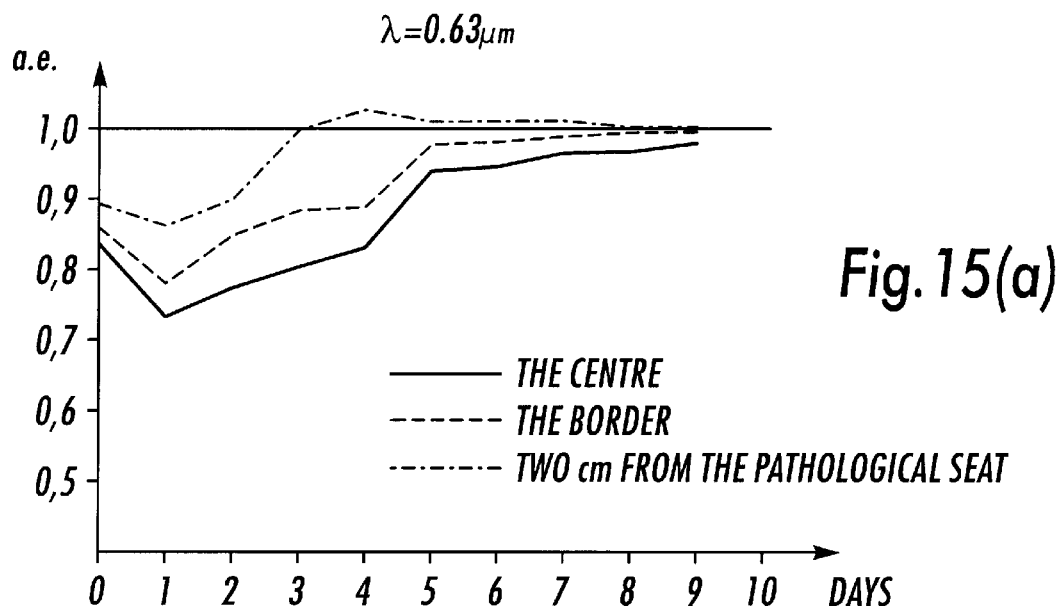
FIGS. 15a to 15f are graphs of an optical index which varies during treatment of inflammatory, dystrophical or oncological conditions.
Figure 15B:
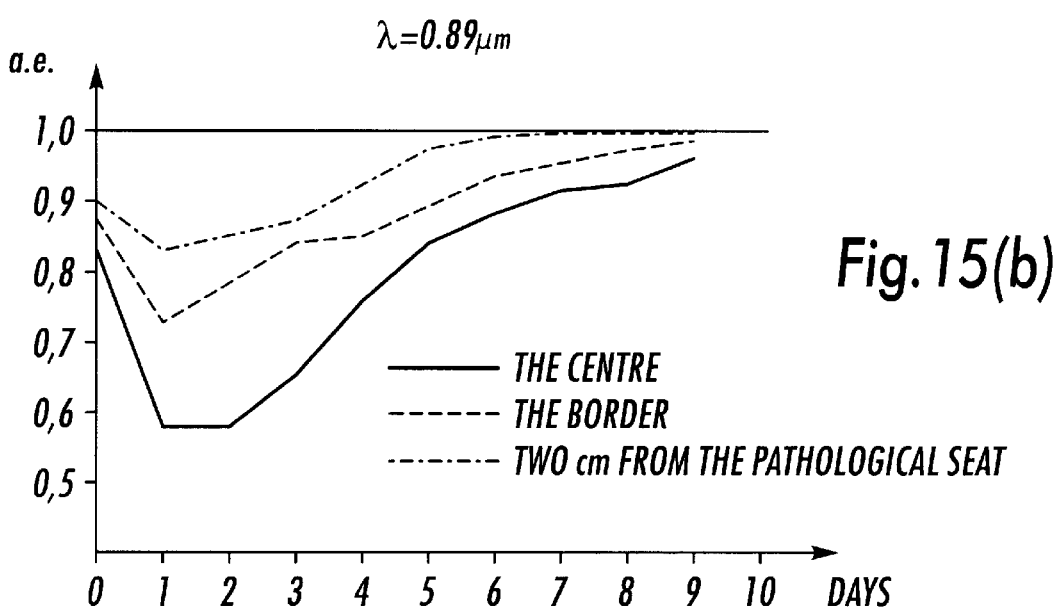
Figure 15C:
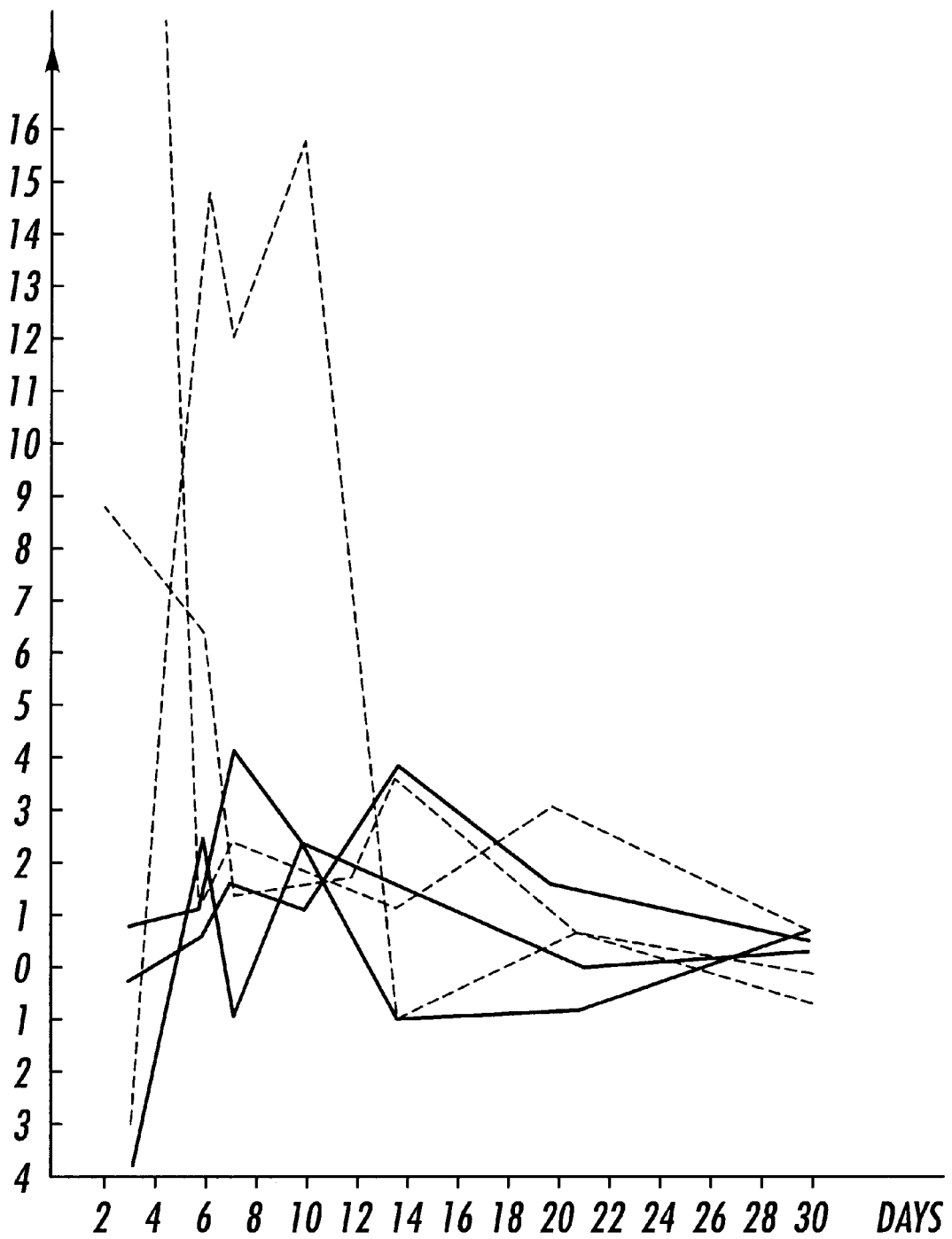
Figure 15D:
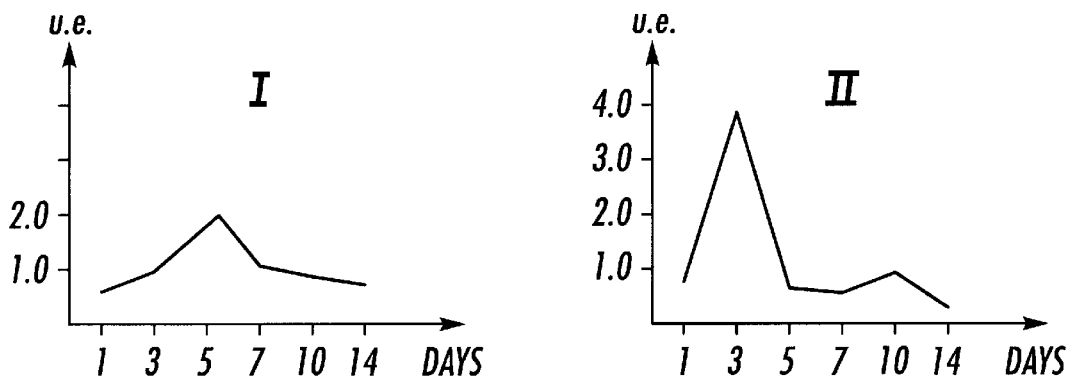
Figure 15E:
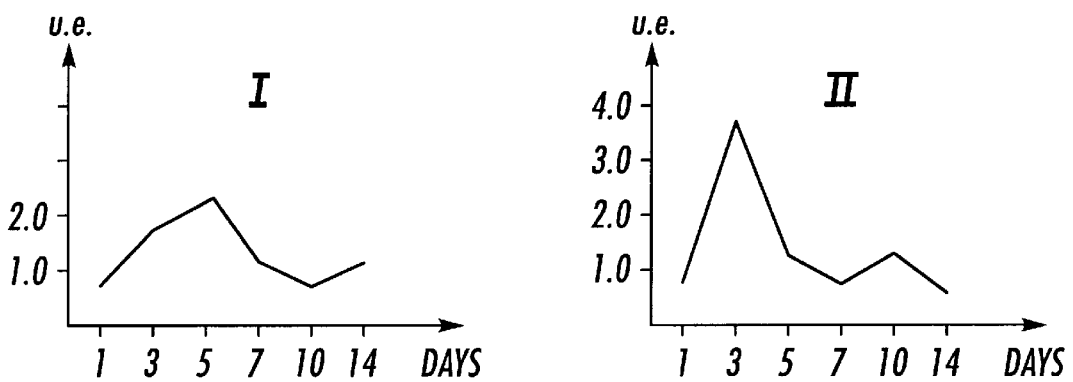
Figure 15F:
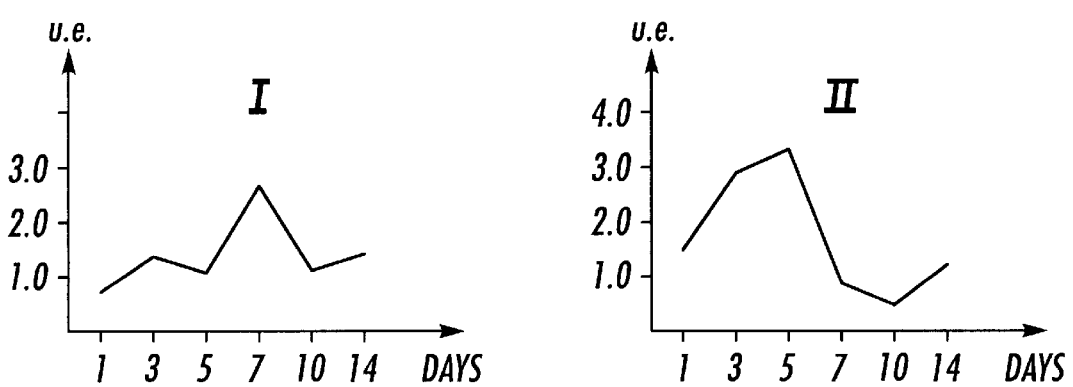

Using the apparatus of the invention, any recognised form of surgery and/or therapy can be carried out until the standardised optical parameters obtained correspond to those for intact tissue at every point in the region previously determined to be pathological. FIGS. 15a to 15j show graphical examples of such treatment. FIGS. 15a and 15b show treatment of inflammatory tissue in a 42 year old patient, FIG. 15c shows laser therapy for a facial fracture and FIGS. 15d to 15f show treatment of Flagmon's jaw.

Control of the photodynamic therapy can also be carried out using lasering PNC-diagnostic. The intensities of stimulated radiation for intact tissue, $T_{fi}$ and at the centre, $T_{fc}$ and limits $T_{fl}$ of the pathological area are measured, these values having been previously set for a reflection coefficient of 1. If $T_{fc}/T_{fi} \geq 2.5$, and if $T_{fc} > T_{fl} > T_{fi}$, then photodynamic therapy is commenced. During such therapy, the ratio $T_{fc}/T_{fi}$ is monitored simultaneously and continuously. If it stabilises, or if its sign changes for 10 seconds within an error margin of 5% or less the treatment is interrupted and is repeated when $T_{fc} > 1.5-2.5$, but not earlier than 24 hours after. The patient's recovery can be determined when the equation $T_{fc}=T_{fl}=T_{fi}$ is satisfied.

Figure 15G:
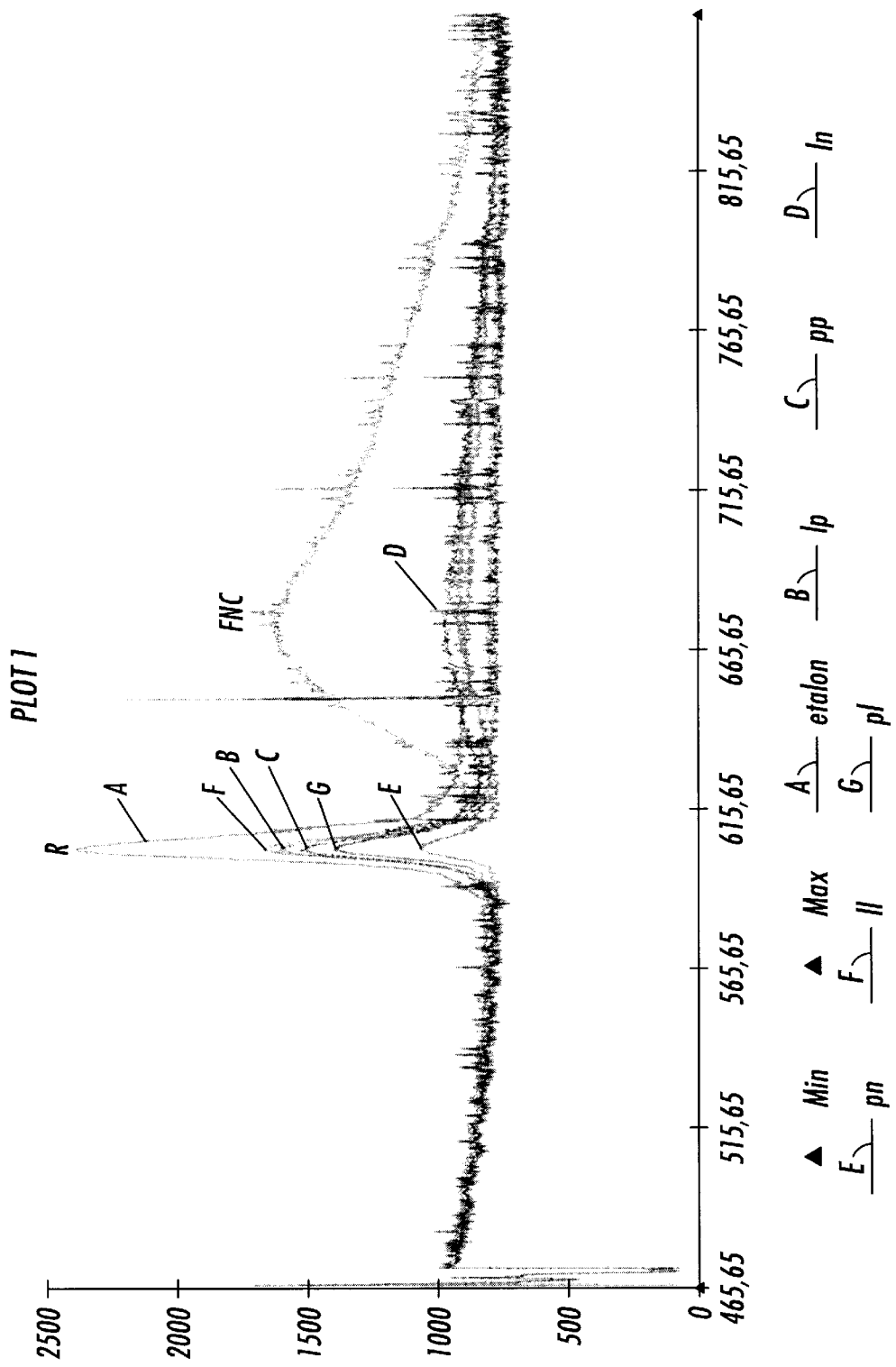
Figure 15H:
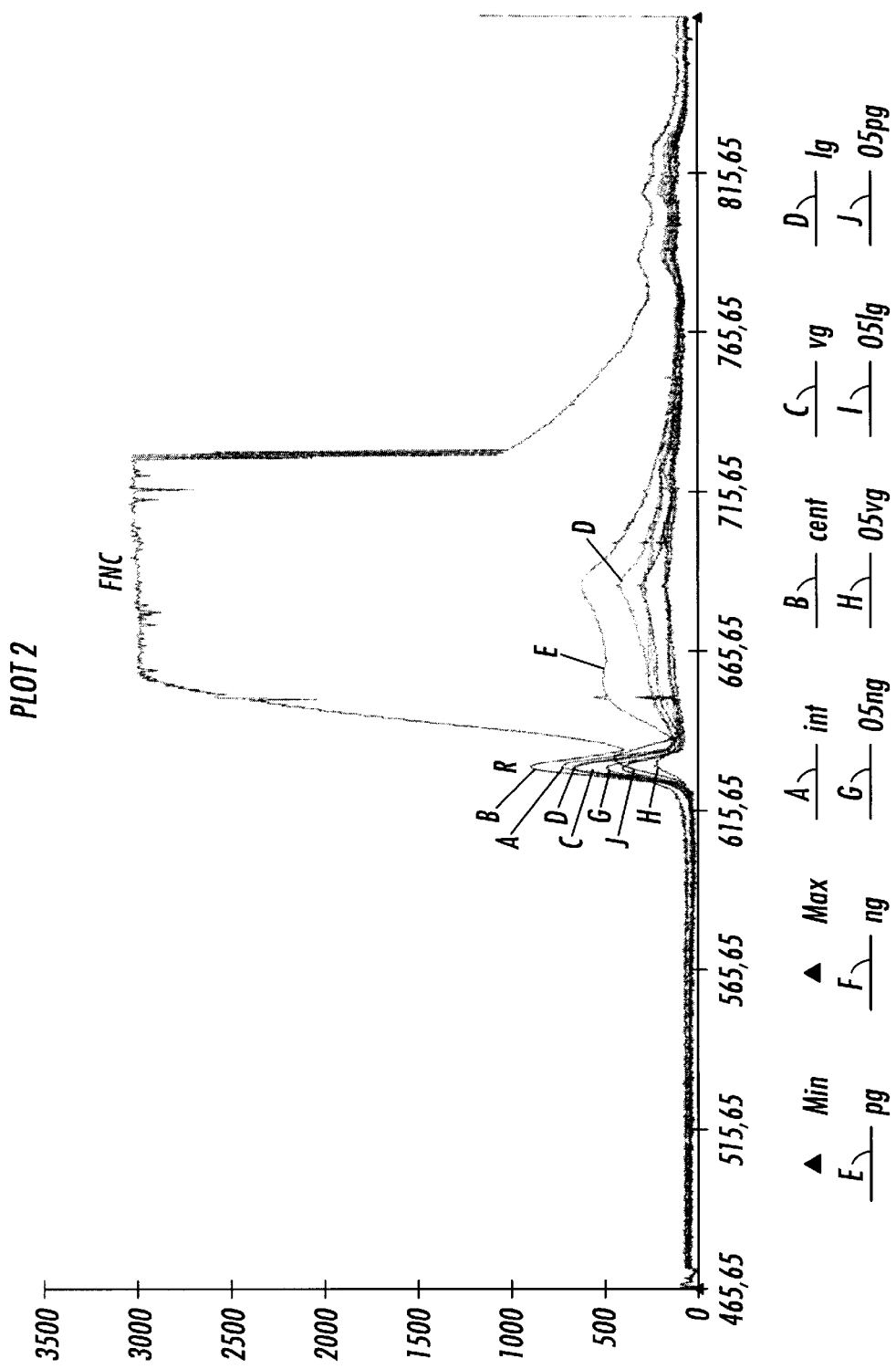

FIGS. 15g–15j demonstrate examples of such treatment. FIG. 15g depicts spectral distributions of the reflected (R) and stimulated (PNC) signals with the photodynamical therapy being performed:before photosense injection (g); on the second day after the photosense injection (h); 15 minutes after the laser irradiation start (0.63 μm) (i); 20 minutes after the laser irradiation start (j). After a sharp decrease of the PNC-signal from the lesion and after its recurrent increase, the photodynamical therapy should be stopped.

In the method of treatment of oncological diseases the lesion is subjected to radiant therapy using radiomodifying and protection properties of low and high intensity laser radiation, electromagnetic fields and other ways, increasing microcirculation and tissue oxygenation and, consequently, increasing radiosensitivity of the lesion and at the same time decreasing radiation damages, local radiant reactions on the side of normal surrounding tissues, even if the total lesion dose of the radiant therapy is increased. Effective parameters of external effects are individual for every patient, this being so, their choice and optimisation should be brought about under control of the claimed diagnostic apparatus.

Specifically, when gamma therapy is used, combined with low intensity laser irradiation, the course of treatment should not last less than three days. The laser treatment starts from irradiation with power density 7 to 220 mW/cm² and fluency 0.1–0.2 J/cm², the blood flow pulse-signal dynamical increase in the irradiation area should be under control (e.g. the lesion tissue oxygenation increase).

The laser treatment is kept on until the blood flow pulse-signal intensity and/or oxygenation in the irradiation area, having reached their maximum, start dropping, within time-period of 10 seconds and more. Immediately after every effective dose of low intensity laser irradiation, the distant gamma therapy should be started and should last 6–25 minutes. The number of treatments should be defined by histological indices normalization (3 and more). In cases where the blood flow-pulse signal increase and/or tissue oxygenation are not observed, the method should not be implemented.

Another way of lesion treatment by means of gamma-radiation resides in the preliminary measurement of the PNC-signal from the lesion and in subsequent synchronisation of its proliferative activity with e.g. 5-florouracil in the course of 3–5 days and in daily registration of the PNC-signals from lesion (Tfi,Tfc,Tfl). When the PNC-signal is absent, the preparation taking should be stopped, the PNC-signal should therewith arise again and, with constraint $T_{fi} > T_{fc} > T_{fl}$, 1.5–2, the gamma therapy should be started. The gamma radiation treatment should be performed daily, with the course not shorter than 3 days long. Recovery of oncological patients in all methods of treatment is defined as $1.05 < c < 1.15$ and/or $T_{fi} = T_{fc} = T_{fl}$.

Figure 15K:
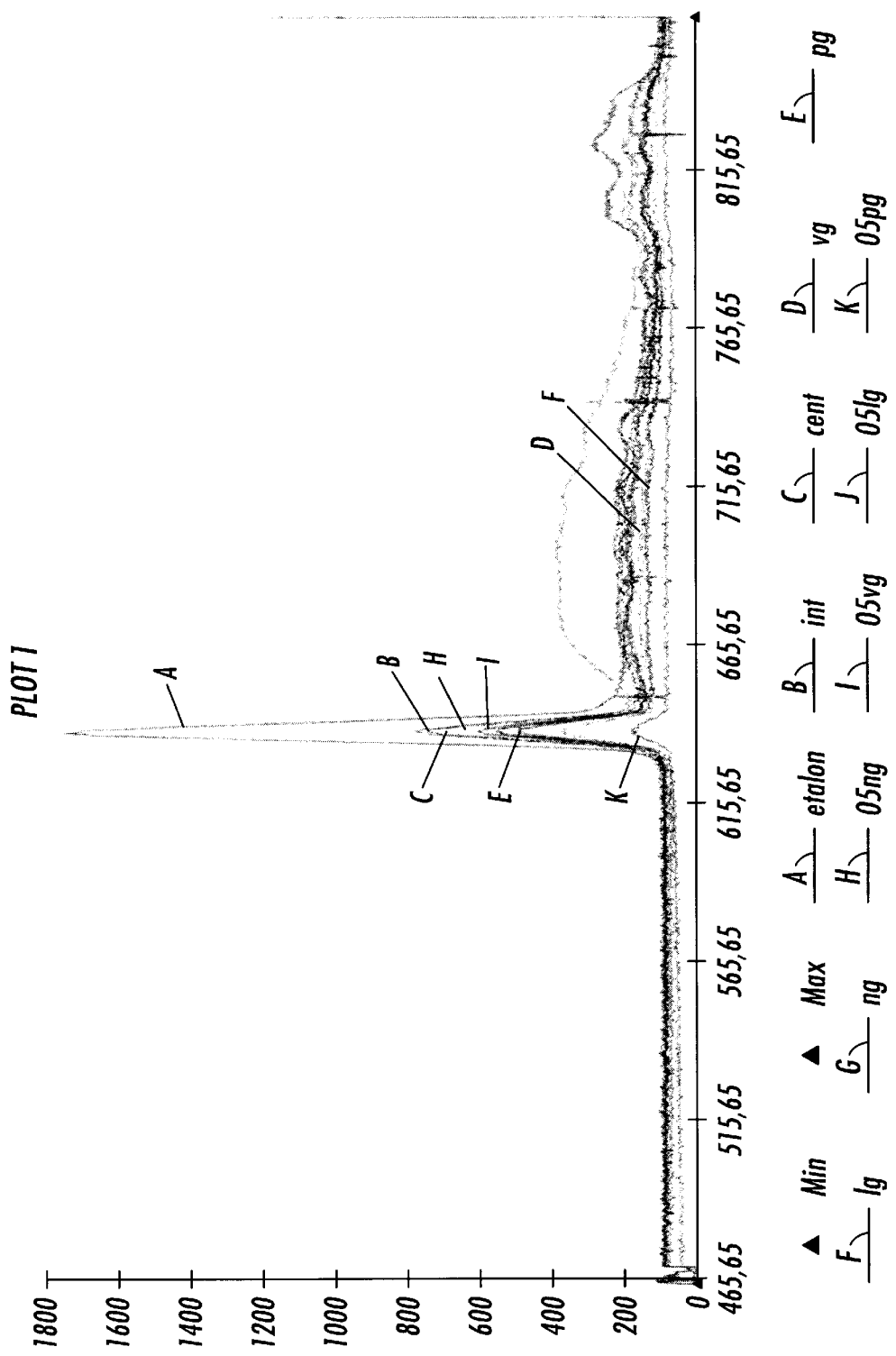

FIGS. 15k–15m demonstrate an example of such treatment. FIG. 15k depicts spectral distributions of the reflected (R) and stimulated (PNC) signals before 5-fluorouracil injection. On the fourth day after injection the proliferative activity was blocked and the PNC-signal in FIG. 15l is virtually absent. On the second day after the 5-fluorouracilum treatment withdrawal the PNC signal appeared again and the course of gamma-therapy was immediately restarted.

A specific method of treating inflammatory, dystrophical or tumoral conditions will now be described. Firstly the pathological area is determined using the device of FIG. 8. The probing radiation reflection coefficient is then found and the energy exposure may be set as follows:

| | |
|---|---|
| Dense erythrocytes setting (RES)/ preliminary tissue preparation | 0.2 J/cm² |
| Suppurative RES | 0.5 J/cm² |
| Necrotic tissue | 0.78 J/cm² |
| Tumoral tissue | 30 to 300 J/cm² |

The duration of the treatment is determined by $$t \text{ (sec)} = \frac{DS}{P(1 - \rho - \tau)}$$

where D is the energy exposure in J/Cm²,

S is the pathological area in cm²,

P is the probing radiation power in W and $\rho$ and $\tau$ are the coefficients of reflection and transparency, respectively.

The apparatus is then switched on to carry out this treatment which is repeated either daily or twice daily with an interval of 3 to 6 hours between the two sessions. The treatment is completed when the equation $$\frac{\rho_{PATHOLOGICAL}}{\rho_{REPER}} = \frac{\rho_{INTACT}}{\rho_{REPER}} = \text{constant}$$

is satisfied for a period of 1 to 2 days. FIGS. 16a and 16c show an example of such a course of treatment for probing radiation of wavelength 0.63 μm for the points on a human hand shown in FIG. 16b.

FIGS. 17a to 17c show examples of diagnosis of different pathological processes using probing radiation of wavelength 0.63 μm.

The probing radiation itself can be used to achieve various therapeutic effects. For example, for light having a wavelength of 0.63 μm the following power ranges can be used:

| | |
|---|---|
| Achieving anti-inflammatory effect | 100 to 200 mW/cm² |
| Stimulating microcirculation | 100 to 250 mW/cm² |
| Stimulating tissue regeneration | 0.1 to 220 mW/cm² |
| Inhibiting tissue microflora and cell proliferation | 400 to 800 mW/cm² |
| Photodynamic therapy | 30000 to 50000 mW/cm² |

Described herein is a dermabrasion method realised with the aid of the apparatus of the invention. In the beginning, parameters C, Tfi, Tfc, Tfl should be measured inside the operation area. Then, the dermabrasion, by means of pulsed laser radiation in the scanning SilkTouch mode, is used to have C decreased by 5% at least. The said indices should be measured daily in the course of 2–3 days and in case Tfi=Tfc=Tfl and if the difference between this value and initial values of all three parameters lay in the corridor +/−5%, the treatment should be terminated. With deep wrinkles treatment, after primary processing, index C drops by 5–10% and the value Tfi=Tfc=Tfl is 1.5–20 times higher than initial ones. When the indicated changes of T are absent, the processing should be repeated, but not earlier than 3 days after the start of the treatment. To make the rehabilitation process after the dermabrasion shorter, the probing radiation of the apparatus of invention is used to achieve different therapeutic effects.

The apparatus of the invention can be used to treat inflammatory and oncological diseases of the prostate as shown in FIG. 18a. In this case, the probing radiation device 2 is formed as a flexible urethrical catheter, the distal end of which includes a device for rotating the radiation beam about is optical axis, where the probing and surgical radiation coincide. The material of the catheter re-reflects radiation in the optical range and the catheter is used for diagnostic, physically therapeutic and surgical purposes. After switching on the probing radiation source 1, the catheter is inserted into the urethra and ultrasonic sensors and/or stimulated radiation is monitored to determine the presence, dimensions and degree of the pathological process. The method of surgical and therapeutic treatment can then be decided and these two treatments are carried out simultaneously. The duration and number of sessions is determined by the rate at which the index of stimulated radiation approaches that of intact tissue.

Alternatively, as shown in FIG. 18b, the surgical treatment can be carried out using the urethrical catheter and the physically therapeutic treatment can be performed using a rectal catheter.

It will be appreciated that the invention can be used in surgery, dermatology, endoscopy, stomatology, radiology, veterinary medicine, oncology, paediatrics and other fields.

The implementation area and the principles of application of the indicated parameters of laser irradiation brought about with the aid of the device described in the present invention have been tested and can be implemented for diagnostics and treatment of purulent injuries, tropical ulcers in grown-ups and children, fractures, osteomyelitis, anal ulcers, anal fissures, oral ulcer-erosion injuries, gullet, stomach and intestine, neurodermatitis, eczema, multi-form exudative erythema, lupoid ulcer, fever sore, localised itch, erosion-ulcer genitalia lesions, tonsillitis, otitis, paradontium, gingivitis, Menkersson-Rosental syndrome, ischemic heart disease, hypertensive disease, hepatitis, biliary cirrhosis, definition of viability of the tissue.

While the invention has been described with reference to a preferred embodiment it will be understood by those skilled in the art that various changes may be made and equivalents may be substituted for elements thereof without departing from the scope of the invention as claimed. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

Concepts, developing in the present invention are realised as a number of computerised treatment diagnostic complexes and PNC-OLIVER systems in particular.

Conceptions developing in the present invention are realised as a number of computerised treatment diagnostic complexes and PNC-OLIVER systems in particular. work algorithm of this program of the above system is noticed in the appendix A. Obviously that algorithms for particular nosology forms can be done as a number of other computer programs.

What is claimed is:

1. Diagnostic apparatus comprising:
   (a) a source (1) of probing electromagnetic radiation
   (b) means (2) for transmitting the output from the probing radiation source (1) to biological tissue (3) to be examined
   (c) means (4, 41) for detecting probing radiation reflected from the tissue (3) and stimulated radiation resulting from excitation of the tissue (3) by the probing radiation
   (d) processing means (5–9) responsive to the reflected and stimulated radiations to produce a signal for diagnosis of the condition of the tissue, and
   (e) means (15, 16) for regulating the intensity of the probing radiation including a feedback circuit (16, 17, 18) for controlling the regulating means (15) and responsive to the intensity of the reflected and stimulated radiation.

2. Diagnostic apparatus as claimed in claim 1, wherein the regulating means comprises a polarising device (15) for varying the intensity of the radiation emitted by the probing radiation source (1), drive means (18) for adjusting the polarising device, and a sensor (17) arranged to be responsive to the reflected and stimulated radiations, said drive means (18) being responsive to the sensor so as to adjust the polarising device and vary the intensity of the probing radiation.

3. Diagnostic apparatus as claimed in claim 2, wherein the source of probing electromagnet radiation produces an output defining an optical axis, and including an optical divider (16) disposed on the optical axis for directing a fraction of the reflected and stimulated radiations to the sensor (17) which is located remotely from the optical axis.

4. Diagnostic apparatus as claimed in claim 1, wherein the probing radiation source is a laser source (1) and the means for regulating the intensity of the probing radiation comprises a partial mirror (16) disposed at the rear of the laser source, said partial mirror transmitting a fraction of the radiation from the source to a sensor (17) which is responsive to the radiation and actuates a regulating device (18) controlling the transparency of the mirror so as to adjust the radiation transmitted therethrough and therefore the intensity of the probing radiation emitted by the laser source.

5. Diagnostic apparatus as claimed in claim 1, wherein the feedback circuit (16,17,18) includes circuit means for effecting a fast, stepped, coarse adjustment of the regulating means and a precision tuning circuit means.

6. Diagnostic apparatus as claimed claim 1, wherein the feedback circuit (16,17,18) includes means for manually adjusting the regulating means (15,16).

7. Diagnostic apparatus as claimed in claim 1, wherein the processing means includes spectral attenuating means (5) for varying the absolute and relative intensities of the reflected and stimulated radiations.

8. Diagnostic apparatus as claimed in claim 1, wherein the processing means includes a monochromator (6) for processing the reflected and stimulated radiations.

9. Diagnostic apparatus as claimed in claim 8 including focusing means (35) located between the spectral attenuator (5) and the monochromator (6) for independently focusing the reflected and stimulated radiations on to a dispersive element (33) of the monochromator, said focusing means being adapted to regulate the diameter of the reflected and stimulated radiation beams at the surface of the dispersive element, and an optical ruler (34) on to which the beams are reflected by the dispersive element.

10. Diagnostic apparatus as claimed in claim 1 wherein the probing radiation source comprises a source (1) for producing optical radiation within the electromagnetic spectrum.

11. Diagnostic apparatus as claimed in claim 10, wherein the source for producing optical radiation comprises a laser source (1) of probing radiation and includes a laser (10a), a spectral element (11) for dividing the radiation emitted by the laser (10a) into a number of discrete spectral components within the bandwidth of the laser, a selection device (12) for selecting discrete spectral components of the radiation, whereby the wavelengths of the probing radiation are adjustable in order to obtain information from different depths in the biological tissue (3) being examined and to which the different wavelengths can penetrate, said selection device (12) also controlling the intensity and physical location of the discrete components, and a wavelength mixer (13) for combining the selected radiation components for launching into the transmitting means (2).

12. Diagnostic apparatus as claimed in claim 1 wherein the probing radiation source (1) produces a wave tunable in the band between 0.3–25 μm.

13. Diagnostic apparatus as claimed in claim 1, wherein at least one of the transmitting means (2) and the detecting means (4) comprise fibre optic means.

14. Diagnostic apparatus as claimed in claim 13, including means (21, 22, 36) for coupling the fibre optic means to the tissue (3) to be examined and for regulating the distance of the output and input ends thereof from the tissue.

15. Diagnostic apparatus as claimed in claim 1, including calibrating means (10) adapted to supply the detecting means (4) with radiation signals simulating reflected and stimulated radiation attainable from biological tissue having different healthy and pathological conditions to produce standardised signals, and means for transmitting the standardised signals to the processing means (7) for comparison with real time signals.

16. Diagnostic apparatus as claimed in claim 15, wherein the calibrating means (10) includes interchangeable plates, each of which has optical characteristics simulating tissue, and wherein the calibrating means is operable to cause the probing radiation emitted from the output of the transmitting means (2) to be incident on a selected plate of the calibration means such that the resulting reflected and stimulated radiation is sensed by the detecting means (4).

17. Diagnostic apparatus as claimed in claim 1, including means for determining the boundaries of pathological tissue and wherein the processing means is coupled to the means for determining the boundaries of pathological tissue.

18. Diagnostic apparatus as claimed in claim 1, wherein the processing means includes a visual display device (8) for displaying an image of the area of tissue under examination.

19. Diagnostic apparatus as claimed in claim 1, wherein the means (2) for probing signal transmission and means (4, 41) for probing tissue (3) signal detection detecting probing and stimulating radiation are incorporated in means (31) located at a given distance from the surface plane of biological tissue to obtain salient features of the anathomotopographical zone under survey.

20. Diagnostic apparatus as claimed in claim 1 wherein the means (2) for transmitting the output from the probing radiation source and the means (4, 41) for detecting probing and stimulating radiation are incorporated in means (31), comprising a space scanner producing visual images of discrete pathological spots and graphical diagrams of lesions showing increased or decreased activity of cells on the background of healthy bio-tissues.

21. Diagnostic apparatus as claimed in claim 1, incorporating external means (42) designed to regulate the intensity of the stimulated radiation on the tissue (3) under survey.

22. Diagnostic apparatus as claimed in claim 21 wherein external means (42) is a source emitting one of beta and gamma radiation onto the tissue under survey.

23. Diagnostic apparatus as claimed in claim 21 wherein external means (42) is a source, radiating in band 0.2 to 11 $\mu$m.

24. Diagnostic apparatus as claimed in claim 21 wherein external means (42) regulates at least one of the surface temperature and the temperature inside the volume of the tissue (3) under survey.

25. Diagnostic apparatus as claimed in claim 21 wherein external means (42) regulates stimulated radiation intensity on the basis of at least one of electrical, optical, magnetic, chemical and biological input.

26. Diagnostic apparatus as claimed in claim 21 wherein external means (42) regulates stimulated radiation intensity on the basis of injection of medicinal preparations.

27. Diagnostic apparatus as claimed in claim 1 including a photoplethysmograph means (45) for measuring microcirculation and oxygenation of the tissue and a therapeutic optical radiation dosimeter, and wherein the output of the photoplethysmograph operates to control the therapeutic optical radiation dosimeter.

28. Diagnostic apparatus as claimed in claim 1 incorporating means (46) presenting medical visualisation of at least one of interior and surface structures of a living organism.

29. Diagnostic apparatus as claimed in claim 28, incorporating means (46) for obtaining and superposing images selected from visual, Roentgen, ultrasonic, magnetic-resonance, thermographic, radio-nucleus and computer-tomographic diagnostic images on a single display (48) with the object of at least one of consecutive and joint tissue diagnostic survey.

30. Diagnostic apparatus as claimed in claim 1 wherein the means (2) for transmitting the output from the probing radioactive source (1) and the means (4, 41) for detecting probing and stimulating radiation are incorporated in means (49) used to perform biopsy tests and to produce signals in the mode of the interstitial tissue diagnostics.

31. Diagnostic apparatus as claimed in claim 1 in combination with apparatus for treating tissue including laser means (44) for treating the tissue under examination by the diagnostic apparatus.

32. Diagnostic apparatus as claimed in claim 1 in combination with apparatus for treating tissue incorporating means (44), comprising a radioactive source for performing radial therapy, means for measuring microcirculation and tissue oxygenation, means for tissue oxygenation stimulation with the object of overcoming resistance and controlling radiomodifying properties of hypoxic lesion cells.

33. Diagnostic apparatus as claimed in claim 32, wherein the means for tissue oxygenation stimulation comprises an optical source, radiating in band 0.4 to 11 $\mu$m.

34. Diagnostic apparatus as claimed in claim 32, wherein the means for tissue oxygenation stimulation comprises at least one of electrical and magnetic field source.

35. Diagnostic apparatus as claimed in claim 32, wherein the means for tissue oxygenation stimulation comprises at least one of a compression chamber for breathing and a local generator of oxygen and at least one of oxygen derivatives and oxygen containing mixture in the lesion area.

36. Diagnostic apparatus as claimed in claim 32, wherein the means for tissue oxygenation stimulation comprises medical injection of vasodilating preparations.

37. Diagnostic apparatus as claimed in claim 1 incorporating an elipticity-meter for defining at least one of roughness, turgor and humidity and biological objects on the noncontact basis.

38. A method of diagnosing the condition of biological tissue (3), comprising the steps of impinging electromagnetic radiation on the tissue, detecting probing radiation reflected from the tissue and stimulated radiation resulting from excitation of the tissue by the probing radiation, processing the reflected and stimulated radiations to produce a signal identifying the condition of the tissue, monitoring the intensity of the probing radiation by sensing a fraction of the reflected and stimulated radiations, and regulating the intensity of the probing radiation in response to the intensity of said fraction.

39. A method as claimed in claim 38 in combination with a method of treating tissue including the steps of treating the tissue under diagnosis and repeating the diagnosis and treatment until the tissue is diagnosed as normal.

40. A method as claimed in claim 39, including the steps of producing standardised signals corresponding to the intensities of the probing and stimulated radiations, measuring within a pathological area of the tissue, at least one of inflammatory, dystrophic and oncological activity by comparing reflection coefficients of reflected and stimulated radiations in real time with the standardised signals, and conducting treatment by periodically obtaining the reflection coefficients of the reflected and stimulated radiations and comparing their rate of change with database information.

41. A method of defining the state of biological tissue (3), using apparatus including a source of probing electromagnetic radiation, means for transmitting an output from the source of probing electromagnetic radiation to biological tissue to be examined, and means for detecting probing radiation reflected from the tissue and stimulated radiation resulting from excitation of the tissue by the probing radiation, and including the steps of:

(a) transmitting a probing signal comprising probing radiation from the source of probing electromagnetic radiation to biological tissue to be examined, (b) detecting probing radiation reflected from the tissue and stimulated radiation resulting from excitation of the tissue by the probing radiation, (c) modulating amplitude, frequency and temporal characteristics of the probing signal, and (d) step-by-step analysis, and amplitude, frequency and temporal characteristics processing of the tissue reflected probing signal and the signal stimulated by the probing irradiation, and of variations invoked by modulation of the characteristics of the probing signal, to define the state of the biological tissue.

42. A method of defining the state of biological tissue (3), using apparatus including a source of probing electromagnetic radiation, means for transmitting an output from the source of probing electromagnetic radiation to biological tissue to be examined, and means for detecting probing radiation reflected from the tissue and stimulated radiation resulting from excitation of the tissue by the probing radiation, and including the steps of:

(a) transmitting a probing signal comprising probing radiation from the source of probing electromagnetic radiation to biological tissue to be examined, (b) detecting probing radiation reflected from the tissue and stimulated radiation resulting from excitation of the tissue by the probing radiation, (c) modulating amplitude, frequency and temporal characteristics of external means, regulating intensity of the stimulated radiation, and (d) step-by-step analysis, and amplitude, frequency and temporal characteristics processing of the tissue reflected probing signal and the signal stimulated by the probing irradiation, and of variations invoked by modulation of the characteristics of the external means, to define the state of the biological tissue.

43. A method of defining the state of biological tissue (3), using apparatus including a source of probing electromagnetic radiation, means for transmitting an output from the source of probing electromagnetic radiation to biological tissue to be examined, and means for detecting probing radiation reflected from the tissue and stimulated radiation resulting from excitation of the tissue by the probing radiation, and including the steps of:

(a) transmitting a probing signal comprising probing radiation from the source of probing electromagnetic radiation to biological tissue to be examined and the probing signal further comprising a fixed band wave scanning in accordance with at least one of definite and random control, (b) detecting probing radiation reflected from the tissue and stimulated radiation resulting form excitation of the tissue by the probing radiation, and (c) step-by-step dynamic analysis of the stimulated signal characteristic frequencies and amplitude peak-value displacements due to the probing signal fixed band wave scanning to define the state of the biological tissue.

44. A method of defining the state of biological tissue (3) and radiant therapy for treating the tissue, using apparatus including a source of probing electromagnetic radiation, means for transmitting an output from the source of probing electromagnetic radiation to biological tissue to be examined, means for detecting probing radiation reflected from the tissue and stimulated radiation resulting from excitation of the tissue by the probing radiation, a radioactive source for performing radiant therapy, and means for tissue oxygenation stimulation, and the process of defining the state of biological tissue including the steps of:

(a) transmitting a probing signal comprising probing radiation from the source of probing electromagnetic radiation to biological tissue to be examined, (b) detecting probing radiation reflected from the tissue and stimulated radiation resulting from excitation of the tissue by the probing radiation, the process of radiant therapy including the steps of:

(c) performing oxygenation stimulation to reach maximal oxygen concentration in tissue with subsequent radiant therapy and (d) repeating steps a) through c) until the tissue is diagnosed as normal.

* * * * *